(12) United States Patent
Gallagher et al.

(10) Patent No.: US 7,595,315 B2
(45) Date of Patent: Sep. 29, 2009

(54) MORPHOLINE DERIVATIVES AS NOREPINEPHRINE REUPTAKE INHIBITORS

(75) Inventors: Peter Thaddeus Gallagher, Basingstoke (GB); Carlos Lamas-Peteira, Alcobnedas (ES); Francisco Javier Agejas-Chicharro, Alcobnedas (ES)

(73) Assignee: Eli Lilly and Company, Indianapolis, IN (US)

( * ) Notice: Subject to any disclaimer, the term of this patent is extended or adjusted under 35 U.S.C. 154(b) by 557 days.

(21) Appl. No.: 10/575,469

(22) PCT Filed: Dec. 10, 2004

(86) PCT No.: PCT/US2004/038240

§ 371 (c)(1),
(2), (4) Date: Apr. 12, 2006

(87) PCT Pub. No.: WO2005/066144

PCT Pub. Date: Jul. 21, 2005

(65) Prior Publication Data

US 2007/0060585 A1    Mar. 15, 2007

(30) Foreign Application Priority Data

Dec. 23, 2003    (EP) .................................. 03380306

(51) Int. Cl.
*A61K 31/5375*    (2006.01)
*C07D 265/30*    (2006.01)

(52) U.S. Cl. .................... 514/239.5; 544/174; 544/106; 544/173

(58) Field of Classification Search ................ 544/106, 544/174, 173; 514/239.5
See application file for complete search history.

(56) References Cited

FOREIGN PATENT DOCUMENTS

| WO | WO 01/01973 | 1/2001 |
|---|---|---|
| WO | WO 2004/017977 | 3/2004 |
| WO | WO 2004/018441 | 3/2004 |

*Primary Examiner*—Rebecca L Anderson
(74) *Attorney, Agent, or Firm*—Tonya L. Combs; Charles E. Cohen; Thomas E. Jackson

(57) ABSTRACT

Compounds of the general formula (I)

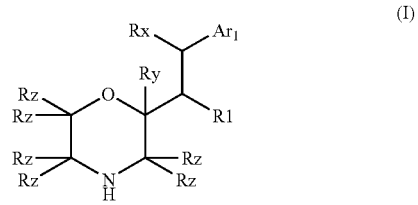

are inhibitors of the reuptake of norepinephrine. As such, they may be useful for the treatment of disorders of the central and/or peripheral nervous system.

3 Claims, No Drawings

MORPHOLINE DERIVATIVES AS NOREPINEPHRINE REUPTAKE INHIBITORS

This invention relates to novel morpholine compounds, and to their use in selectively inhibiting norepinephrine reuptake.

Selective inhibition of norepinephrine reuptake is a relatively new mode of action for the treatment of affective disorders. Norepinephrine appears to play an important role in the disturbances of vegetative function associated with affective, anxiety and cognitive disorders. Atomoxetine hydrochloride is a selective inhibitor of norepinephrine reuptake, and is marketed for the treatment of attention deficit hyperactivity disorder (ADHD). Reboxetine is also a selective norepinephrine reuptake inhibitor, and is marketed for the treatment of depression. WO99/15177 discloses the use of Reboxetine to treat ADHD and WO01/01973 discloses the use of S,S-Reboxetine to treat inter alia ADHD.

According to the present invention there is provided a compound of formula (I)

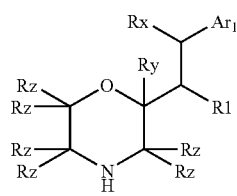

wherein,

Rx is H or C1-C4 alkyl;

Ry is H or C1-C4 alkyl;

each Rz group is independently H or C1-C4 alkyl, with the proviso that not more than 3 Rz groups may be C1-C4 alkyl;

R1 is C1-C6 alkyl (optionally substituted with 1, 2 or 3 halogen atoms and/or with 1 substituent selected from C1-C4 alkylthio (optionally substituted with 1, 2 or 3 fluorine atoms), C1-C4 alkoxy (optionally substituted with 1, 2 or 3 fluorine atoms), C3-C6 cycloalkoxy, C1-C4 alkylsulfonyl, cyano, —CO—O(C1-C2 alkyl), —O—CO—(C1-C2 alkyl) and hydroxy); C2-C6 alkenyl (optionally substituted with 1, 2 or 3 halogen atoms); C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C=C bond; C4-C7 cycloalkylalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C=C bond; or $(CH_2)_n Ar2$ wherein n is 0 or 1; and Ar1 and Ar2 are each independently a phenyl ring or a 5- or 6-membered heteroaryl ring each of which is optionally substituted with 1, 2 or 3 substituents (depending upon the number of available substitution positions) each independently selected from C1-C4 allkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo and hydroxy and/or with 1 substituent selected from pyridyl, thiophenyl, phenyl, benzyl and phenoxy each of which is optionally ring-substituted with 1, 2 or 3 substituents each independently selected from halogen, C1-C4 alkyl (optionally substituted with 1, 2 or 3 halogen atoms), C1-C4 alkoxy (optionally substituted with 1, 2 or 3 halogen atoms), carboxy, nitro, hydroxy, cyano, —NRR, —CONRR, $SO_2NRR$ and $SO_2R$); and each R is independently H or C1-C4 alkyl;

or a pharmaceutically acceptable salt thereof.

In the present specification the term "C1-C4 alkyl" means a monovalent unsubstituted saturated straight-chain or branched-chain hydrocarbon radical having from 1 to 4 carbon atoms. Thus the term "C1-C4 alkyl" includes, for example, methyl, ethyl, n-propyl, isopropyl, n-butyl, isobutyl, sec-butyl and tert-butyl.

In the present specification the term "C1-C4 alkoxy" means a monovalent unsubstituted saturated straight-chain or branched-chain hydrocarbon radical having from 1 to 4 carbon atoms linked to the point of substitution by a divalent O radical. Thus the term "C1-C4 alkoxy" includes, for example, methoxy, ethoxy, n-propoxy, isopropoxy, n-butoxy, isobutoxy, sec-butoxy and tert-butoxy.

In the present specification the term "C1-C4 alkylthio" means a monovalent unsubstituted saturated straight-chain or branched-chain hydrocarbon radical having from 1 to 4 carbon atoms linked to the point of substitution by a divalent S radical. Thus the term "C1-C4 alkylthio" includes, for example, methylthio, ethylthio, n-propylthio, isopropylthio, n-butylthio, isobutylthio, sec-butylthio and tert-butylthio.

In the present specification the term "C3-C6 cycloalkyl" means a monovalent unsubstituted saturated cyclic hydrocarbon radical having from 3 to 6 carbon atoms. Thus the term "C3-C6 cycloalkyl" includes, for example, cyclopropyl, cyclobutyl, cyclopentyl and cyclohexyl.

In the present specification the term "C4-C7 cycloalkylalkyl" means a monovalent unsubstituted saturated cyclic hydrocarbon radical having from 3 to 6 carbon atoms linked to the point of substitution by a divalent unsubstituted saturated straight-chain or branched-chain hydrocarbon radical having at least 1 carbon atom. Thus the term "C4-C7 cycloalkyl" includes, for example, cyclopropylmethyl, cyclopropylethyl, cyclobutylmethyl, cyclopentylmethyl and cyclohexylmethyl.

In the present specification the phrase "wherein one C—C bond within the cycloalkyl moiety is optionally substituted by an O—C, S—C or C=C bond" means that either (i) any two adjacent carbon atoms within a cycloalkyl ring may be linked by a double bond rather than a single bond (with the number of substituents on each carbon atom being reduced accordingly), or that (ii) one of any two adjacent C atoms within a cycloalkyl ring (and any substituents thereon) may be replaced by an oxygen or sulphur atom. Examples of groups encompassed by this phrase when used in conjunction with the term C3-C6 cycloalkyl include, for example:

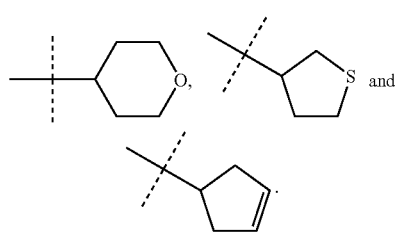

Examples of groups encompassed by this phrase when used in conjunction with the term C4-C7 cycloalkylalkyl include, for example:

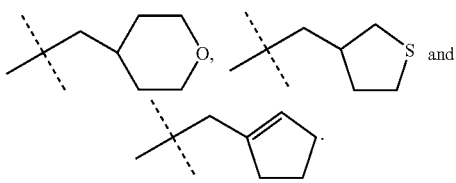

In the present specification the term "C2-C6 alkenyl" means a monovalent unsubstituted unsaturated straight-chain or branched-chain hydrocarbon radical having from 2 to 6 carbon atoms and containing at least one carbon-carbon double bond. Thus the term "C1-C4 alkenyl" includes, for example, ethenyl, propenyl, 2-methyl-2-propenyl and butenyl.

In the present specification the term "C3-C6 cycloalkoxy" means a monovalent unsubstituted saturated cyclic hydrocarbon radical having from 3 to 6 carbon atoms in the ring linked to the point of substitution by a divalent O radical. Thus the term "C3-C6 cycloalkoxyl" includes, for example, cyclopropoxy.

In the present specification the term "C1-C4 alkylsulfonyl" means a monovalent unsubstituted saturated straight-chain or branched-chain hydrocarbon radical having from 1 to 4 carbon atoms linked to the point of substitution by a divalent $SO_2$ radical. Thus the term "C1-C4 alkylsulfonyl" includes, for example, methylsulfonyl.

In the present specification terms similar to the above definitions specifying different numbers of C atoms take an analogous meaning.

In the present specification the term "halo" or "halogen" means F, Cl, Br or I.

In the present specification the term "phenoxy" means a monovalent unsubstituted phenyl radical linked to the point of substitution by a divalent O radical.

In the present specification the term "5-membered heteroaryl ring" means a 5-membered aromatic ring including one or more heteroatoms each independently selected from N, O and S. Preferably there are not more than three heteroatoms in total in the ring. More preferably there are not more than two heteroatoms in total in the ring. More preferably there is not more than one heteroatom in total in the ring. The term includes, for example, the groups thiazolyl, isothiazolyl, oxazolyl, isoxazolyl, thiophenyl, furanyl, pyrrolyl, imidazolyl, triazolyl, oxadiazolyl and thiadiazolyl.

"Thiazolyl" as used herein includes 2-thiazolyl, 4-thiazolyl and 5-thiazolyl.

"Isothiazolyl" as used herein includes 3-isothiazolyl, 4-isothiazolyl, and 5-isothiazolyl.

"Oxazolyl" as used herein includes 2-oxazolyl, 4-oxazolyl and 5-oxazolyl.

"Isoxazolyl" as used herein includes 3-isoxazolyl, 4-isoxazolyl, and 5-isoxazolyl.

"Thiophenyl" as used herein includes 2-thiophenyl and 3-thiophenyl.

"Furanyl" as used herein includes 2-furanyl and 3-furanyl.

"Pyrrolyl" as used herein includes 1-pyrrolyl, 2-pyrrolyl and 3-pyrrolyl.

"Imidazolyl" as used herein includes 1-imidazolyl, 2-imidazolyl and 4-imidazolyl.

"Triazolyl" as used herein includes 1-thiazolyl, 4-triazolyl and 5-triazolyl.

"Oxadiazolyl" as used herein includes 4- and 5-(1,2,3-oxadiazolyl), 3- and 5-(1,2,4-oxadiazolyl), 3-(1,2,5-oxadiazolyl), 2-(1,3,4-oxadiazolyl).

"Thiadiazolyl" as used herein includes 4- and 5-(1,2,3-thiadiazolyl), 3- and 5-(1,2,4-thiadiazolyl), 3-(1,2,5-thiadiazolyl), 2-(1,3,4-thiadiazolyl).

In the present specification the term "6-membered heteroaryl ring" means a 6-membered aromatic ring including one or more heteroatoms each independently selected from N, O and S. Preferably there are not more than three heteroatoms in total in the ring. More preferably there are not more than two heteroatoms in total in the ring. More preferably there is not more than one heteroatom in total in the ring. The term includes, for example, the groups pyridyl, pyrimidyl, pyrazinyl, pyridazinyl and triazinyl.

"Pyridyl" as used herein includes 2-pyridyl, 3-pyridyl and 4-pyridyl.

"Pyrimidyl" as used herein includes 2-pyrimidyl, 4-pyrimidyl and 5-pyrimidyl.

"Pyrazinyl" as used herein includes 2-pyrazinyl and 3-pyrazinyl.

"Pyridazinyl" as used herein includes 3-pyridazinyl and 4-pyridazinyl.

"Triazinyl" as used herein includes 2-(1,3,5-triazinyl), 3-, 5- and 6-(1,2,4-triazinyl) and 4- and 5-(1,2,3-triazinyl).

In the present specification the term "ortho" refers to a position on the Ar1 aromatic ring which is adjacent to the position from which Ar1 links to the rest of the compound of formula (I).

In a preferred embodiment of the present invention, Rx is H or methyl. Most preferably Rx is H.

In a preferred embodiment of the present invention, Ry is H or methyl. Most preferably Ry is H.

In a preferred embodiment of the present invention, each Rz group is independently H or methyl, with the proviso that not more than 3 Rz groups may be methyl. Most preferably, each Rz is H.

In a preferred embodiment of the present invention, R1 is C1-C6 alkyl (optionally substituted with 1, 2 or 3 halogen atoms and/or with 1 substituent selected from C1-C4 alkylthio (optionally substituted with 1, 2 or 3 fluorine atoms), C1-C4 alkoxy (optionally substituted with 1, 2 or 3 fluorine atoms), C3-C6 cycloalkoxy, C1-C4 alkylsulfonyl, cyano, —CO—O(C1-C2 alkyl), —CO—(C1-C2 alkyl) and hydroxy). More preferably, R1 is C1-C6 alkyl (optionally substituted with 1, 2 or 3 halogen atoms and/or with 1 substituent selected from C1-C4 alkoxy (optionally substituted with 1, 2 or 3 fluorine atoms), cyano and hydroxy). More preferably, R1 is C1-C6 alkyl (optionally substituted with 1, 2 or 3 halogen atoms). More preferably, R1 is C1-C6 alkyl (optionally substituted with 1, 2 or 3 fluorine atoms). Examples of specific identities for R1 within this embodiment include methyl, ethyl, iso-propyl, iso-butyl, 3,3,3-trifluoropropyl and 4,4,4-trifluorobutyl.

In a preferred embodiment of the present invention, R1 is C2-C6 alkenyl (optionally substituted with 1, 2 or 3 halogen atoms).

In a preferred embodiment of the present invention, R1 is C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C=C bond. More preferably, R1 is C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C bond. More preferably, R1 is C3-C6 cycloalkyl wherein one C—C bond within the cycloalkyl moiety is optionally substituted by an O—C bond. Examples of specific identities for R1 within this embodiment include cyclopropyl, cyclopentyl and tetrahydropyranyl (in particular tetrahydro-2H-pyran-4-yl).

In a preferred embodiment of the present invention, R1 is C4-C7 cycloalkylalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C=C bond.

In a preferred embodiment of the present invention, R1 is $(CH_2)_n$Ar2 wherein n is 1 and wherein Ar2 is as defined above. More preferably, R1 is $CH_2$Ar2 wherein Ar2 is a phenyl ring or a pyridyl (preferably 2-pyridyl) ring each of which may be substituted with 1, 2 or 3 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo and hydroxy. More preferably, R1 is $CH_2$Ar2 wherein Ar2 is a phenyl ring optionally substituted in the manner described in the preceding sentence. More preferably, R1 is $CH_2$Ar2 wherein Ar2 is a phenyl ring optionally substituted with 1 or 2 substituents each independently selected from C1-C4 alkyl (optionally substituted with 1, 2 or 3 halogen atoms), C1-C4 alkoxy (optionally substituted with 1, 2 or 3 halogen atoms), halo and hydroxy. Examples of specific identities for R1 within this embodiment include phenylmethyl and (2-methoxy-phenyl)methyl.

In a preferred embodiment of the present invention, R1 is $(CH_2)_n$Ar2 wherein n is 0 and wherein Ar2 is as defined above. More preferably, R1 is a phenyl ring or a pyridyl (preferably 2-pyridyl) ring each of which may be substituted with 1, 2 or 3 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo and hydroxy. More preferably, R1 is a phenyl ring optionally substituted in the manner described in the preceding sentence. More preferably, R1 is a phenyl ring optionally substituted with 1 or 2 substituents each independently selected from C1-C4 alkyl (optionally substituted with 1, 2 or 3 halogen atoms), C1-C4 alkoxy (optionally substituted with 1, 2 or 3 halogen atoms), halo and hydroxy. Most preferably R1 is an unsubstituted phenyl ring.

In a preferred embodiment of the present invention, Ar1 is an unsubstituted phenyl ring or or an unsubstituted 5- or 6-membered heteroaryl ring. More preferably, Ar1 is an unsubstituted phenyl ring or an unsubstituted pyridyl (preferably 2-pyridyl) ring.

In a preferred embodiment of the present invention, Ar1 is a phenyl ring or a 5- or 6-membered heteroaryl ring; each of which is substituted in the ortho position with a substituent selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo, hydroxy, pyridyl, thiophenyl, phenyl, benzyl and phenoxy, each of which ortho substituents is optionally ring-substituted (where a ring is present) with 1, 2 or 3 substituents each independently selected from halogen, C1-C4 alkyl (optionally substituted with 1, 2 or 3 halogen atoms), C1-C4 alkoxy (optionally substituted with 1, 2 or 3 halogen atoms), carboxy, nitro, hydroxy, cyano, —NRR, —CONRR, $SO_2$NRR and $SO_2$R; and each of which is (in addition to ortho substitution) optionally further substituted with 1 or 2 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo and hydroxy. More preferably, Ar1 is a phenyl ring or a pyridyl (preferably 2-pyridyl) ring each of which is substituted and optionally further substituted in the manner described in the preceding sentence. More preferably, Ar1 is a group of the formula (a):

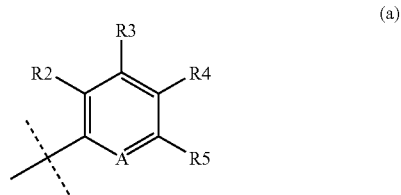

wherein,

A is N or CR6 (preferably CR6); R2 is C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo, hydroxy, pyridyl, thiophenyl, phenyl (optionally substituted with 1, 2 or 3 substituents each independently selected from halogen, C1-C4 alkyl (optionally substituted with 1, 2 or 3 halogen atoms), or C1-C4 alkoxy (optionally substituted with 1, 2 or 3 halogen atoms)) or phenoxy (optionally substituted with 1, 2 or 3 halogen atoms); R3 is H; R4 is H; R5 is H, C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo or hydroxy; and R6 (if present) is H. More preferably, Ar1 is a group of the formula (a) wherein, A is CR6; R2 is C1-C4 alkyl (optionally substituted with 1, 2 or 3 fluorine atoms), C1-C4 alkoxy (optionally substituted with 1, 2 or 3 fluorine atoms), phenyl (optionally substituted with 1, 2 or 3 substituents each independently selected from fluorine and trifluoromethoxy), pyridyl (preferably 3-pyridyl) or phenoxy; R3 is H; R4 is H; R5 is H or F; and R6 is H. Examples of specific identities for Ar1 include 2-isopropyl-phenyl, 2-trifluoromethyl-phenyl, 2-methoxy-phenyl, 2-ethoxy-phenyl, 2-trifluoromethoxy-phenyl, 2-phenyl-phenyl, 2-(3-fluoro-phenyl)-phenyl, 2-(4-fluoro-phenyl)-phenyl, 2-(3-trifluoromethoxy-phenyl)-phenyl, 2-(4-trifluoromethoxy-phenyl)-phenyl, 2-phenoxy-phenyl, 2-pyridyl-phenyl, 2-methoxy-5-fluoro-phenyl, 2-trifluoromethoxy-5-fluoro-phenyl and 2-phenyl-5-fluoro-phenyl.

It will be appreciated that a compound of formula (I) above will possess at least two asymmetric carbon atoms. In the present specification, where a structural formula does not specify the stereochemistry at one or more chiral centres, it encompasses all possible stereoisomers and all possible mixtures of stereoisomers (including, but not limited to, racemic mixtures), which may result from stereoisomerism at each of the one or more chiral centers. In a preferred embodiment of the present invention, there is provided a compound of formula (II)

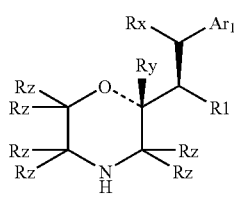

(II)

wherein, Rx, Ry, Rz, R1 and Ar1 are as defined for formula (I) above; or a pharmaceutically acceptable salt thereof.

In a preferred embodiment of the present invention, there is provided a compound of formula (III)

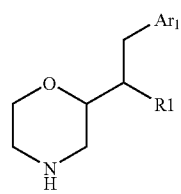

(III)

wherein, R1 and Ar1 are as defined for formula (I) above; or a pharmaceutically acceptable salt thereof.

In a preferred embodiment of the present invention, there is provided a compound of formula (III) wherein R1 is C1-C6 alkyl (optionally substituted with 1, 2 or 3 halogen atoms and/or with 1 substituent selected from C1-C4 alkylthio (optionally substituted with 1, 2 or 3 fluorine atoms), C1-C4 alkoxy (optionally substituted with 1, 2 or 3 fluorine atoms), C3-C6 cycloalkoxy, C1-C4 alkylsulfonyl, cyano, —CO—O(C1-C2 alkyl), —O—CO—(C1-C2 alkyl) and hydroxy); C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C═C bond; or $(CH_2)_n$Ar2 wherein n is 0 or 1 and Ar2 is a phenyl ring or a pyridyl (preferably 2-pyridyl) ring each of which may be substituted with 1, 2 or 3 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo and hydroxy; and Ar1 is a phenyl ring or a 5'- or 6-membered heteroaryl ring; each of which is substituted in the ortho position with a substituent selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo, hydroxy, pyridyl, thiophenyl, phenyl, benzyl and phenoxy, each of which ortho substituents is optionally ring-substituted (where a ring is present) with 1, 2 or 3 substituents each independently selected from halogen, C1-C4 alkyl (optionally substituted with 1, 2 or 3 halogen atoms), C1-C4 alkoxy (optionally substituted with 1, 2 or 3 halogen atoms), carboxy, nitro, hydroxy, cyano, —NRR, 'CONRR, $SO_2$NRR and $SO_2$R; and each of which is (in addition to ortho substitution) optionally further substituted with 1 or 2 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo and hydroxy; or a pharmaceutically acceptable salt thereof.

In a preferred embodiment of the present invention, there is provided a compound of formula (IV)

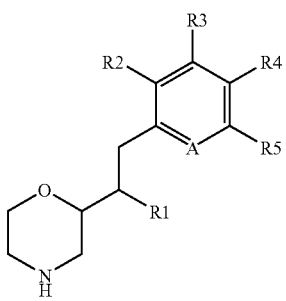

(IV)

wherein,

R1 is $(CH_2)_n$Ar2 wherein n is 0 or 1 and Ar2 is a phenyl ring or a pyridyl (preferably 2-pyridyl) ring each of which may be substituted with 1, 2 or 3 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo and hydroxy; A is N or CR6 (preferably CR6); R2 is C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo, hydroxy, pyridyl, thiophenyl, phenyl (optionally substituted with 1, 2 or 3 substituents each independently selected from halogen, C1-C4 alkyl (optionally substituted with 1, 2 or 3 halogen atoms), or C1-C4 alkoxy (optionally substituted with 1, 2 or 3 halogen atoms)) or phenoxy (optionally substituted with 1, 2 or 3 halogen atoms); R3 is H; R4 is H; R5 is H, C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo or hydroxy; and R6 (if present) is H; or a pharmaceutically acceptable salt thereof.

In a preferred embodiment of the present invention, there is provided a compound of formula (V)

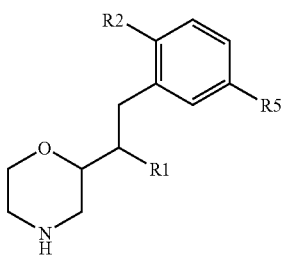

(V)

wherein,

R1 is (CH$_2$)$_n$Ar2 wherein n is 0 and Ar2 is a phenyl ring optionally substituted with 1 or 2 substituents each independently selected from C1-C4 alkyl (optionally substituted with 1, 2 or 3 halogen atoms), C1-C4 alkoxy (optionally substituted with 1, 2 or 3 halogen atoms), halo and hydroxy;

R2 is C1-C4 alkyl (optionally substituted with 1, 2 or 3 fluorine atoms), C1-C4 alkoxy (optionally substituted with 1, 2 or 3 fluorine atoms), phenyl (optionally substituted with 1, 2 or 3 substituents each independently selected from fluorine and trifluoromethoxy), pyridyl (preferably 3-pyridyl) or phenoxy; and R5 is H or F;

or a pharmaceutically acceptable salt thereof.

In a preferred embodiment of the present invention, there is provided a compound of formula (VI)

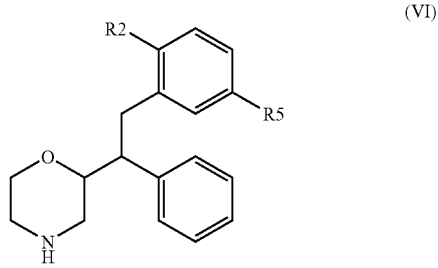

(VI)

wherein,

R2 is C1-C4 alkyl (optionally substituted with 1, 2 or 3 fluorine atoms), C1-C4 alkoxy (optionally substituted with 1, 2 or 3 fluorine atoms), phenyl (optionally substituted with 1, 2 or 3 substituents each independently selected from fluorine and trifluoromethoxy), pyridyl (preferably 3-pyridyl) or phenoxy; and R5 is H or F;

or a pharmaceutically acceptable salt thereof.

The compounds of the present invention are inhibitors of norepinephrine reuptake. Biogenic amine transporters control the amount of biogenic amine neurotransmitters in the synaptic cleft. Inhibition of the respective transporter leads to a rise in the concentration of that neurotransmitter within the synaptic cleft. Compounds of formula (I) and their pharmaceutically acceptable salts preferably exhibit a $K_i$ value less than 600 nM at the norepinephrine transporter as determined using the scintillation proximity assay described below. More preferred compounds of formula (I) and their pharmaceutically acceptable salts exhibit a $K_i$ value less than 100 nM at the norepinephrine transporter. More preferred compounds of formula (I) and their pharmaceutically acceptable salts exhibit a $K_i$ value less than 50 nM at the norepinephrine transporter. Especially preferred compounds of formula (I) and their pharmaceutically acceptable salts exhibit a $K_i$ value less than 20 nM at the norepinephrine transporter. Preferably, compounds of the present invention selectively inhibit the norepinephrine transporter relative to the serotonin and dopamine transporters by a factor of at least five, more preferably by a factor of at least ten using the scintillation proximity assays described below.

In addition, the compounds of the present invention are preferably acid stable. Advantageously, they have a reduced interaction (both as substrate and inhibitor) with the liver enzyme Cytochrome P450 (CYP2D6). That is to say, they preferably exhibit less than 75% metabolism via the CYP2D6 pathway according to the CYP2D6 substrate assay described below and they preferably exhibit an IC50 of >6 μM according to the CYP2D6 inhibitor assay described below.

In view of their pharmacological activity, the compounds of the present invention are indicated for the treatment of disorders of the central and/or peripheral nervous system, in particular, disorders associated with norepinephrine dysfunction in mammals, especially humans, including children, adolescents and adults.

The term "norepinephrine dysfunction" as used herein refers to a reduction in the amount of norepinephrine neurotransmitter within the synaptic cleft below that which would be considered to be normal or desirable for a species, or an individual within that species. Thus the phrase "disorders associated with norepinephrine dysfunction in mammals" refers to disorders which are associated with a reduction in the amount of norepinephrine neurotransmitter within the synaptic cleft below that which would be considered to be normal or desirable for the mammalian species, or an individual within the species, in question. Disorders associated with norepinephrine dysfunction in mammals include, for example, nervous system conditions selected from the group consisting of an addictive disorder and withdrawal syndrome, an adjustment disorder (including depressed mood, anxiety, mixed anxiety and depressed mood, disturbance of conduct, and mixed disturbance of conduct and mood), an age-associated learning and mental disorder (including Alzheimer's disease), alcohol addiction, allergies (in particular allergic rhinitis), anorexia nervosa, apathy, asthma, an attention-deficit disorder (ADD) due to general medical conditions, attention-deficit hyperactivity disorder (ADHD) including the predominantly inattentive type of ADHD and the predominantly hyperactive-impulsive type of ADHD (and optionally by way of combination therapy with one or more stimulants such as methylphenidate, amphetamine and dextroamphetamine), bipolar disorder, bulimia nervosa, chronic fatigue syndrome, chronic or acute stress, cognitive disorders (discussed in more detail below but including mild cognitive impairment (MCI) and cognitive impairment associated with schizophrenia (CIAS)), communication disorders (including stuttering, expressive language disorder, mixed receptive-expressive language disorder, phonological disorder and communication disorder not otherwise specified), conduct disorder, cyclothymic disorder, dementia of the Alzheimers type (DAT), depression (including adolescent depression and minor depression), dysthymic disorder, emotional dysregulation (including emotional dysregulation associated with ADHD, borderline personality disorder, bipolar disorder, schizophrenia, schizoaffective disorder and intermittent explosive disorder), fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder, hot flashes or vasomotor symptoms, hypotensive states including orthostatic hypotension, impulse control disorders (including intermittent explosive disorder, kleptomania, pyromania, pathological gambling, trichotillomania and impulse-control disorder not otherwise specified), incontinence (i.e., bedwetting, stress incontinence, genuine stress incontinence, and mixed incontinence), an inhalation disorder, an intoxication disorder, learning disabilities (including developmental speech and language disorders (such as developmental articulation disorder, developmental expressive language disorder and developmental receptive language disorder), learning disorders (such as reading disorder, mathematics disorder, disorder of written expression and learning disorder not otherwise specified) and motor skills disorders (such as developmental coordination disorder)), mania, migraine headaches, neuropathic pain, nicotine addiction, obesity (i.e., reducing the weight of obese or overweight patients), obsessive compulsive disorders and related spectrum disorders, oppositional defiant disorder, pain including chronic pain, neuropathic pain and antinociceptive pain, panic disorder, Parkinson's disease (in particular to improve dyskinesia, oscilations, balance, coordination, depression, and motivation), peripheral neuropathy, personality change due to a general medical condition (including labile type, disinhibited type, aggressive type, apathetic type, paranoid type, combined type and unspecified type), pervasive developmental disorders (including autistic disorder, Asperger's disorder, Rett's disorder, childhood disintegrative disorder, and pervasive developmental disorder not otherwise specified), post-traumatic stress disorder, premenstrual dysphoric disorder (i.e., premenstrual syndrome and late luteal phase dysphoric disorder), psoriasis, psychoactive substance use disorders, a psychotic disorder (including schizophrenia, schizoaffective and schizophreniform disorders), seasonal affective disorder, a sleep disorder (such as narcolepsy and enuresis), social phobia (including social anxiety disorder), a specific developmental disorder, selective serotonin reuptake inhibition (SSRI) "poop out" syndrome (i.e., wherein a patient who fails to maintain a satisfactory response to SSRI therapy after an initial period of satisfactory response), TIC disorders (e.g., Tourette's Disease), tobacco addiction and vascular dementia.

The term "cognitive disorders" (also variously referred to as "cognitive failure," "cognitive insufficiency," "cognitive deficit," "cognitive impairment," "cognitive dysfunction," and the like) refers to the dysfunction, diminution, or loss of one or more cognitive functions, the processes by which knowledge is acquired, retained, and used. Cognitive dysfunction includes cognitive changes associated with ageing ("age-associated memory impairment"), as well as changes due to other causes. Cognitive impairment is most commonly due to a delirium or dementia, but can also occur in association with a number of other medical or neuropsychiatric disorders. More focal cognitive deficits are diagnosed using the criteria disclosed in the *Diagnostic and Statistical Manual of Mental Disorders*, Fourth Edition, Text Revision (DSM-IV-TR™, 2000), American Psychiatric Association, Washington, D.C., as either amnestic disorders (affecting memory) or cognitive disorder not otherwise specified (NOS), which includes executive dysfunction, visuospatial/visuocontructional impairment, attentional deficits, disorientation, etc. These more focal cognitive disorders also have a wide variety of causes, some of which are of unknown etiology.

A delerium is characterized by a disturbance of consciousness with a reduced ability to focus, sustain, or shift attention and a change in cognition that develops over a short period of time. Delirium is very common, and occurs on average in about a fifth of general hospital inpatients, and is even more common in nursing home patients and those with terminal illnesses. The disorders included in the "Delirium" section of the DSM-IV-TR™ are listed according to presumed etiology: Delirium Due to a General Medical Condition, Substance-Induced Delirium (i.e., due to a drug of abuse, a medication, or toxin exposure), Delirium Due to Multiple Etiologies, or Delirium Not Otherwise Specified (if the etiology is indeterminate). As disclosed by Wise et al. ((2002) Delirium (Confusional States), In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 15, pp. 257-272, Table 154), exemplary etiological bases of delirium include, but are not limited to, infection, withdrawal from alcohol and drugs, acute metabolic conditions, trauma of various types, CNS pathologies, hypoxia, vitamin deficiencies, endocrinopathies, acute vascular conditions, toxins or drugs, and heavy metals.

A dementia is a chronic condition, usually with a more gradual deterioration of memory and other intellectual functioning and other cognitive skills severe enough to interfere with the ability to perform activities of daily living. Although dementia may occur at any age, it primarily affects the elderly, presenting in more than 15% of persons over 65 years of age and in as many as 40% of persons over 80 years old. Dementia due to Alzheimer's disease is particularly common. Non-Alzheimer's cognitive impairments and/or dementias include, for example, those caused by or associated with: vascular diseases; Parkinson's disease; Lewy body disease (diffuse Lewy body disease); HIV/AIDS; mild cognitive impairments; mild nuerocognitive disorders; age-associated memory impairments; neurologic and/or psychiatric conditions including epilepsy and epilepsy treatments; brain tumors, cysts, lesions, or other inflammatory brain diseases; multiple sclerosis; Down's syndrome; Rett's syndrome; progressive supranuclear palsy; frontal lobe dementia syndromes; schizophrenia and related psychiatric disorders; antipsychotic medications; traumatic brain injury (closed head injury), dementia pugilistica, and other head traumas; normal-pressure hydrocephalus; surgery (including coronary artery by-pass graft surgery) and anaesthesia, electroconvulsive shock therapy, and cancer and cancer therapies.

The dementias are also listed in the "Dementia" section of the DSM-IV-TR™ according to presumed etiology: Dementia of the Alzheimer's Type, Vascular Dementia, Dementia Due to Other General Medical Conditions (e.g., human immunodeficiency virus [HIV] disease, head trauma, Parkinson's disease, Huntington's disease), Substance-Induced Persisting Dementia (i.e., due to a drug of abuse, a medication, or toxin exposure), Dementia Due to Multiple Etiologies, or Dementia Not Otherwise Specified (if the etiology is indeterminate). As disclosed by Gray and Cummings ((2002) Dementia, In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 16, pp. 273-306, Table 16-1), exemplary etiological bases of principal dementia syndromes include, but are not limited to, degenerative disorders (cortical and subcortical), vascular disorders, myelinoclastic disorders, traumatic conditions, neoplastic disorders, hydrocephalic disorders, inflammatory conditions, infections, toxic conditions, metabolic disorders, and psychiatric disorders.

An amnestic disorder is characterized by memory impairment in the absence of other significant accompanying cognitive impairments. The disorders in the "Amnestic Disorders" section of the DSM-IV-TR™ are also listed according to presumed etiology: Amnestic Disorder Due to a General Medical Condition, Substance-Induced Persisting Amnestic Disorder, or Amnestic Disorder Not Otherwise Specified.

Cognitive Disorder Not Otherwise Specified in the DSM-IV-TR™ covers presentations that are characterized by cognitive dysfunction presumed to be due to either a general medical condition or substance use that do not meet criteria for any of the disorders listed elsewhere in the section of the DSM-IV-TR™ entitled "Delirium, Dementia, and Amnestic and Other Cognitive Disorders."

Dementia, amnestic disorders, and cognitive disorders NOS occur in patients with a wide variety of other disorders including, but not limited to, Huntington's disease (chorea); Pick's disease; spinocerebellar ataxias (types 1-11); cortico-basalganglionic degeneration; neuroacanthocytosis; dentatorubropallidoluysian atropy (DRPLA); systemic lupus erythematosus; heavy metal intoxication; alcoholic dementia (Wernicke's encephalopathy); fetal alcohol syndrome; single or multiples strokes, including small vessels (Binswanger's dementia: subcortical arteriosclerotic encephalopathy) and large vessels (multi-infarct dementia); anoxic encephalopathy; tumors; birth anoxia; premature birth; inborn errors of metabolism; neurofibromatosis (Type I); tuberous sclerosis; Hallervorden Spatz disease; Wilson's disease; post-infectious sequelae (e.g., tuberculosis, viral encephalitis, bacterial meningitis); subdural hematoma; subcortical dementia; Creutzfeldt-Jakob disease; Gerstmann-Sträussler-Scheinker disease; general paresis; and syphilis.

As discussed in detail above, cognitive failure may present in patients suffering from a number of disorders, including dementia or delirium, or due to a wide variety of other causes. The compounds of the present invention are useful for the treatment or prevention of cognitive failure associated with, or due to, the disorders or etiologies discussed above, including disorders formally classified in the DSM-IV-TR™. For the convenience of the reader, the DSM-IV-TR™ code numbers or descriptions are supplied below. "ICD-9-CM codes" refers to codes for, e.g., selected general medical conditions and medication-induced disorders contained in the *International Classification of Diseases*, 9$^{th}$ Revision, Clinical Modification.

| | |
|---|---|
| Delirium Due to a General Medical Condition | 293.0 |
| Substance-Induced Delirium, including: | |
| Substance Intoxication Delirium: | |
| Code [Specific Substance] Intoxication Delirium: | |
| (291.0 Alcohol; 292.81 Amphetamine [or Amphetamine-Like Substance]; 292.81 | |
| Cannabis; 292.81 Cocaine; 292.81 Hallucinogen; 292.81 Inhalant; 292.81 Opioid; | |
| 292.81 Phencyclidine [or Phencyclidine-Like Substance]; 292.81 Sedative, | |
| Hypnotic, or Anxiolytic; 292.81 Other [or Unknown] Substance [e.g., cimetidine, | |
| digitalis, benztropine]) | |
| Substance Withdrawal Delirium: | |
| Code [Specific Substance] Withdrawal Delirium: | |
| (291.0 Alcohol; 292.81 Sedative, Hypnotic, or Anxiolytic; 292.81 Other [or | |
| Unknown] Substance) | |
| Delirium Due to Multiple Etiologies: | |
| Multiple codes are used, reflecting the specific delirium and specific etiologies, | |
| e.g., 293.0 Delirium Due to Viral Encephalitis; 291.0 Alcohol Withdrawal Delirium | |
| Delirium Not Otherwise Specified | 780.09 |
| Dementia of the Alzheimer's Type | 294.1x* (*ICD-9-CM code) |
| Subtypes: | |
| With Early Onset (onset of the dementia is age 65 years or under) | |
| With Late Onset (onset of the dementia is after age 65 years) | |
| Without Behavioral Disturbance | 294.10 |
| With Behavorial Disturbance | 294.11 |
| Vascular Dementia | 290.4x |
| Subtypes: | |
| With Delirium | 290.41 |
| With Delusions | 290.42 |
| With Depressed Mood | 290.43 |
| With Behavioral Disturbance | Uncoded |
| Uncomplicated | 290.40 |
| Dementia Due to HIV Disease | 294.1x* (*ICD-9-CM code) |
| Dementia Due to Head Trauma | 294.1x* (*ICD-9-CM code) |
| Dementia Due to Parkinson's Disease | 294.1x* (*ICD-9-CM code) |
| Dementia Due to Huntington's Disease | 294.1x* (*ICD-9-CM code) |
| Dementia Due to Pick's Disease | 290.1x* (*ICD-9-CM code) |
| Dementia Due to Creutzfeldt-Jakob Disease | 290.1x* (*ICD-9-CM code) |
| Dementia Due to Other General Medical Conditions | 294.1x* (*ICD-9-CM code) |
| Code based on presence or absence of a clinically significant behavioral | |
| disturbance: | |
| Without Behavioral Disturbance | 294.10 |
| With Behavioral Disturbance | 294.11 |
| Substance-Induced Persisting Dementia | |
| Code [Specific Substance]-Induced Persisting Dementia: | |
| (291.2 Alcohol; 292.82 Inhalant; 292.82 Sedative, Hypnotic, or Anxiolytic; | |
| 292.82 Other [or Unknown] Substance) | |
| Dementia Due to Multiple Etiologies | |
| Coding note: Use multiple codes based on specific dementias and specific | |
| etiologies, e.g., 294.10 Dementia of the Alzheimer's Type, With Late Onset, | |
| Without Behavioral Disturbance; 290.40 Vascular Dementia, Uncomplicated. | |
| Dementia Not Otherwise Specified | 294.8 |
| Amnestic Disorder Due to a General Medical Condition | 294.0 |
| Transient or Chronic | |
| Substance-Induced Persisting Amnestic Disorder | |

-continued

| | |
|---|---|
| Code [Specific Substance]-Induced Persisting Amnestic Disorder:<br>291.1 Alcohol; 292.83 Sedative, Hypnotic, or Anxiolytic; 292.83 Other [or Unknown] Substance | |
| Amnestic Disorder Not Otherwise Specified | 294.8 |
| Cognitive Disorder Not Otherwise Specified | 294.9 |
| Age-Related Cognitive Decline | 780.9 |

Examples of cognitive disorders due to various etiologies, or associated with various disorders, of particular interest that can be prevented or treated using the compounds of the present invention include: enhancing cognitive functions and executive functioning (ability to plan, initiate, organize, carry out, monitor, and correct one's own behavior) in normal subjects or in subjects exhibiting cognitive dysfunction; treatment of cognitive and attentional deficits associated with prenatal exposure to substances of abuse including, but not limited to, nicotine, alcohol, methamphetamine, cocaine, and heroin; treatment of cognitive impairment caused by chronic alcohol and drug abuse (substance-induced persisting dementia), medicament side effects, and treatment of drug craving and withdrawal; treatment of cognitive deficits in Down's Syndrome patients; treatment of deficits in normal memory functioning comorbid with major depressive and bipolar disorders; treatment of cognitive impairment associated with depression, mental retardation, bipolar disorder, or schizophrenia; treatment of dementia syndromes associated with mania, conversion disorder, and malingering; treatment of problems of attention, prefrontal executive function, or memory due to head trauma or stroke; treatment of cognitive dysfunction in menopausal and post-menopausal women and in women undergoing hormone replacement therapy; treatment of cognitive deficits and fatigue due to, or associated with, cancer and cancer therapies (cognitive deficits are associated with a variety of cancer treatments, including cranial radiation, conventional (standard-dose) chemotherapy, high-dose chemotherapy and hematopoietic (bone-marrow) transplantation, and biologic agents).

The invention further provides a method for treating a patient suffering from or susceptible to psychosis, comprising administering to said patient an effective amount of a first component which is an antipsychotic, in combination with an effective amount of a second component which is a compound of formula (I). The invention also provides a pharmaceutical composition that comprises a first component that is an antipsychotic, and a second component that is a compound of formula (I). In the general expressions of this aspect of the present invention, the first component is a compound that acts as an antipsychotic. The antipsychotic may be either a typical antipsychotic or an atypical antipsychotic. Although both typical and atypical antipsychotics are useful for these methods and formulations of the present invention, it is preferred that the first component compound is an atypical antipsychotic.

Typical antipsychotics include, but are not limited to: Chlorpromazine, 2-chloro-10-(3-dimethylaminoprop-yl)phenothiazine, is described in U.S. Pat. No. 2,645,640. Its pharmacology has been reviewed (Crismon, *Psychopharmacol. Bul.,* 4, 151 (October 1967): Droperidol, 1-(1-[3-(p-fluorobenzoyl)propyl]-1,2,3,6-tetrahydro-4-pyridyl)-2-benzimidazolinone, is described in U.S. Pat. No. 3,141,823; Haloperidol, 4-[4-(4-chlorophenyl)-4-hydroxy-1-piperidinyl]-1-(4-fluorophenyl)-1-butanone, is described in U.S. Pat. No. 3,438,991. Its therapeutic efficacy in psychosis has been reported (Beresford and Ward, *Drugs,* 33, 31-49 (1987); Thioridazine, 1-hydroxy-10-[2-(1-methyl-2-pyridinyl)ethyl]-2-(methylthio)phenothiazine hydrochloride, was described by Bourquin, et al. (*Helv. Chim. Acta,* 41, 1072 (1958)). Its use as an antipsychotic has been reported (Axelsson, et al., *Curr. Ther. Res.,* 21, 587 (1977)); and Trifluoperazine, 10-[3-(4-methyl-1-piperazinyl)-propyl]-2-trifluoromethylphenthiazine hydrochloride, is described in U.S. Pat. No. 2,921,069.

Atypical antipsychotics include, but are not limited to: Olanzapine, 2-methyl-4-(4-methyl-1-piperazinyl)-10H-thieno[2,3-b][1,5]benzodiazepine, is a known compound and is described in U.S. Pat. No. 5,229,382 as being useful for the treatment of schizophrenia, schizophreniform disorder, acute mania, mild anxiety states, and psychosis; Clozapine, 8-chloro-11-(4-methyl-1-piperazinyl)-5H-dibenzo[b,e][1,4]diazepine, is described in U.S. Pat. No. 3,539,573. Clinical efficacy in the treatment of schizophrenia is described (Hanes, et al., *Psychopharmacol. Bull.,* 24, 62 (1988)); Risperidone, 3-[2-[4-(6-fluoro-1,2-benzisoxazol-3-yl)piperidino]ethyl]-2-methyl-6,7,8,9-tetrahydro-4H-pyrido[1,2-a]pyrimidin-4-one, and its use in the treatment of psychotic diseases are described in U.S. Pat. No. 4,804,663; Sertindole, 1-[2-[4-[5-chloro-1-(4-fluorophenyl)-1H-indol-3-yl]-1-piperidinyl]ethyl]imidazolidin-2-one, is described in U.S. Pat. No. 4,710,500. Its use in the treatment of schizophrenia is described in U.S. Pat. Nos. 5,112,838 and 5,238,945; Quetiapine, 5-[2-(4-dibenzo[b,f][1,4]thiazepin-11-yl-1-piperazinyl)ethoxy]ethanol, and its activity in assays which demonstrate utility in the treatment of schizophrenia are described in U.S. Pat. No. 4,879,288. Quetiapine is typically administered as its (E)-2-butenedioate (2:1) salt; Ziprasidone, 5-[2-[4-(1,2-benzoisothiazol-3-yl)-1-piperazinyl]ethyl]-6-chloro-1,3-dihydro-2H-indol-2-one, is typically administered as the hydrochloride monohydrate. The compound is described in U.S. Pat. Nos. 4,831,031 and 5,312,925. Its activity in assays which demonstrate utility in the treatment of schizophrenia are described in U.S. Pat. No. 4,831,031; and Aripiprazole (Abilify™), 7-[4-[4-(2,3-dichlorophenyl)-1-piperazinyl]butoxy]-3,4-dihydrocarbostyril (U.S. Pat. Nos. 4,734,416 and 5,006,528) is a new antipsychotic indicated for the treatment of schizophrenia.

It will be understood that while the use of a single antipsychotic as a first component compound is preferred, combinations of two or more antipsychotics may be used as a first component if necessary or desired. Similarly, while the use of a single compound of formula (I) as a second component compound is preferred, combinations of two or more compounds of formula (I) may be used as a second component if necessary or desired. While all combinations of first and second component compounds are useful and valuable, certain combinations are particularly valued and are preferred, as follows:

olanzapine/compound of formula (I)
clozapine/compound of formula (I)
risperidone/compound of formula (I)
sertindole/compound of formula (I)
quetiapine/compound of formula (I)

ziprasidone/compound of formula (I)

aripiprazole/compound of formula (I)

In general, combinations and methods of treatment using olanzapine as the first component are preferred. It is especially preferred that when the first component is olanzapine, it will be the Form II olanzapine as described in U.S. Pat. No. 5,736,541. It is further preferred that the Form II olanzapine polymorph will be administered as the substantially pure Form II olanzapine polymorph. As used herein "substantially pure" refers to Form II associated with less than about 5% Form I, preferably less than about 2% Form I, and more preferably less than about 1% Form I. Further, "substantially pure" Form II will contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water. Although Form II olanzapine is preferred it will be understood that as used herein, the term "olanzapine" embraces all solvate and polymorphic forms unless specifically indicated.

Psychotic conditions that can be treated by the adjunctive therapy aspect of the present invention include schizophrenia, schizophreniform diseases, acute mania, and schizoaffective disorders. The titles given these conditions represent multiple disease states. The following list illustrates a number of these disease states, many of which are classified in the DSM-IV-TR™. The DSM-IV-TR™ code numbers for these disease states are supplied below, when available, for the convenience of the reader.

| | |
|---|---|
| Paranoid Type Schizophrenia | 295.30 |
| Disorganized Type Schizophrenia | 295.10 |
| Catatonic Type Schizophrenia | 295.20 |
| Undifferentiated Type Schizophrenia | 295.90 |
| Residual Type Schizophrenia | 295.60 |
| Schizophreniform Disorder | 295.40 |
| Schizoaffective Disorder | 295.70 |

The present invention also encompasses the use of one or more compounds of formula (I) in combination with one or more conventional Alzheimer's agents for the prevention or treatment of cognitive dysfunction in patients suffering from Alzheimer's disease. Conventional Alzheimer's agents include inhibitors of acetylcholine degradation (i.e., cholinesterase or acetylcholinesterase inhibitors) within synapses, e.g., donepezil (Aricept®), rivastigmine (Exelon®), galantamine (Reminyl®), and tacrine (Cognex®); the selective monoamine oxidase inhibitor selegiline (Eldepryl®); and memantine (Namenda™), a newly FDA-approved NMDA receptor antagonist for the treatment of moderate to severe Alzheimer's disease. Modafinil (Provigil®) is also used in the treatment of Alzheimer's disease.

The present invention also encompasses the use of one or more compounds of formula (I) in combination with one or more conventional Parkinson's agents for the treatment of cognitive dysfunction in Parkinson's disease. Conventional Parkinson's agents include levodopa; levodopa/carbidopa (Sinemet®); Stalevo (carbidopa/levodopa/entacapone); dopamine agonists, e.g., bromocriptine; pergolide; Mirapex® (pramipexole), Permax® (pergolide), and Requip® (ropinirole); COMT inhibitors, e.g., tolcapone, and entacapone; Selegiline (Deprenyl®; Eldepryl®); propranolol; primidone; anticholinergics, e.g., Cogentin®, Artane®, Akineton®, Disipal®, and Kemadrin®; and amantadine.

The compounds of the present invention are particularly suitable for the treatment of attention deficit hyperactivity disorder, ADHD.

The term "treatment" as used herein refers to both curative and prophylactic treatment of disorders associated with norepinephrine dysfunction.

The compounds of the present invention are also indicated for the treatment of disorders which are ameliorated by an increase in the amount of norepinephrine neurotransmitter within the synaptic cleft of a mammal above that which would be considered to be normal or desirable for the mammalian species, or an individual within the species, in question.

In another embodiment of the present invention, there is provided a pharmaceutical composition comprising a compound of formula (I) or a pharmaceutically acceptable salt thereof together with a pharmaceutically acceptable diluent, excipient or carrier.

In another embodiment of the present invention, there is provided a compound of formula (I) or a pharmaceutically acceptable salt thereof for use in therapy.

In another embodiment of the present invention, there is provided a compound of formula (I) or a pharmaceutically acceptable salt thereof for use as an inhibitor of the reuptake of norepinephrine. Preferably such inhibition occurs within mammalian cells (including mammalian cell membrane preparations), especially those found within the central and/or peripheral nervous system. More preferably such inhibition occurs within the cells of the central nervous system of a mammal, especially a human, in need thereof.

In another embodiment of the present invention there is provided a compound of formula (I) or a pharmaceutically acceptable salt thereof for treating disorders associated with norepinephrine dysfunction in mammals.

In another embodiment of the present invention, there is provided the use of a compound of formula (I) or a pharmaceutically acceptable salt thereof for the manufacture of a medicament for inhibiting the reuptake of norepinephrine.

In another embodiment of the present invention, there is provided the use of a compound of formula (I) or a pharmaceutically acceptable salt thereof for the manufacture of a medicament for the treatment of disorders associated with norepinephrine dysfunction in mammals.

In another embodiment of the present invention, there is provided a method for inhibiting the reuptake of norepinephrine in mammals comprising administering to a patient in need thereof an effective amount of a compound of formula (I) or a pharmaceutically acceptable salt thereof.

In another embodiment of the present invention, there is provided a method for treating disorders associated with norepinephrine dysfunction in mammals comprising administering to a patient in need thereof an effective amount of a compound of formula (I) or a pharmaceutically acceptable salt thereof.

The present invention includes the pharmaceutically acceptable salts of the compounds of formula (I). Suitable salts include acid addition salts, including salts formed with inorganic acids, for example hydrochloric, hydrobromic, nitric, sulphuric or phosphoric acids, or with organic acids, such as organic carboxylic or organic sulphonic acids, for example, acetoxybenzoic, citric, glycolic, o-mandelic-l, mandelic-dl, mandelic d, maleic, mesotartaric monohydrate, hydroxymaleic, fumaric, lactobionic, malic, methanesulphonic, napsylic, naphthalenedisulfonic, naphthoic, oxalic, palmitic, phenylacetic, propionic, pyridyl hydroxy pyruvic, salicylic, stearic, succinic, sulfanilic, tartaric, 2-hydroxyethane sulphonic, toluene-p-sulphonic, and xinafoic acids.

The compounds of the present invention may be used as medicaments in human or veterinary medicine. The compounds may be administered by various routes, for example, by oral or rectal routes, topically or parenterally, for example by injection, and are usually employed in the form of a pharmaceutical composition.

Such compositions may be prepared by methods well known in the pharmaceutical art and normally comprise at least one active compound in association with a pharmaceutically acceptable diluent, excipient or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, solutions, syrups, aerosols (as a solid or in a liquid medium), ointments containing, for example, up to 10% by weight of the active compound, soft and hard gelatin capsules, suppositories, injection solutions and suspensions and sterile packaged powders.

Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia, calcium phosphate, alginates, tragacanth, gelatin, syrup, methyl cellulose, methyl- and propylhydrobenzoate, talc, magnesium stearate and mineral oil. The compounds of formula (I) can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. Compositions of the invention may be formulated so as to provide, quick, sustained or delayed release of the active ingredient after administration to the patient by employing procedures well known in the art.

The compositions are preferably formulated in a dosage unit form, each dosage unit containing from about 5 to about 500 mg, more usually about 25 to about 300 mg, of the active ingredient. The term "dosage unit form" refers to physically discrete units suitable as unitary doses for human subjects and other mammals, each unit containing a predetermined quantity of active material calculated to produce the desired therapeutic effect, in association with a suitable pharmaceutical carrier.

Compounds of the present invention may be prepared by conventional organic chemistry techniques. General schemes outlining the synthetic routes to compounds of the present invention are described below. For clarity, R1 is shown as phenyl and Rx, Ry and Rz are shown as H, however, it will be appreciated that analogous methods could be applied for other possible identities of R1, Rx, Ry and Rz.

A key intermediate in routes to compounds of formula (I) is the compound of formula (X), the synthesis of which is outlined in Scheme 1 below. The label "Pg" represents a nitrogen protecting group. Suitable N-protecting groups will be known to the person skilled in the art. Further information on suitable N-protecting groups is contained in the well known text "Protective Groups in Organic Synthesis", Theodora W. Greene and Peter G. M. Wuts, John Wiley & Sons, Inc., New York, 1999, pp. 494-653. Benzyl is an especially preferred N-protecting group.

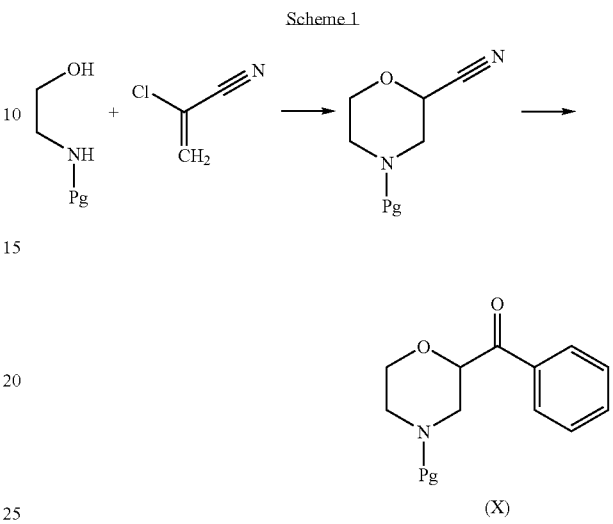

N-protected ethanolamine is reacted with 2-chloroacrylonitrile to provide N-protected morpholine-2-carbonitrile. Reaction of this compound with a suitable organometallic reagent, such as phenylmagnesiumchloride, provides a compound of formula (X).

One possible route to compounds of formula (I) from a compound of formula (X) is shown in Scheme 2 below. In this case the nitrogen protecting group is benzyl (Bn) but in principle other protecting groups would also work. Similarly, the group Ar1 is shown as an ortho-substituted phenyl group but in principle other Ar1 groups could also be used:

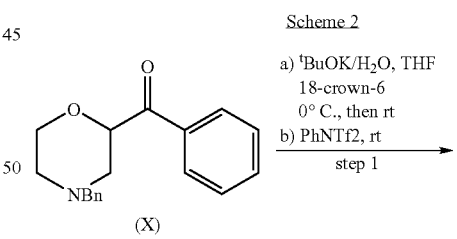

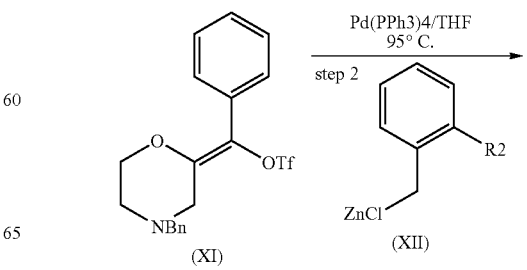

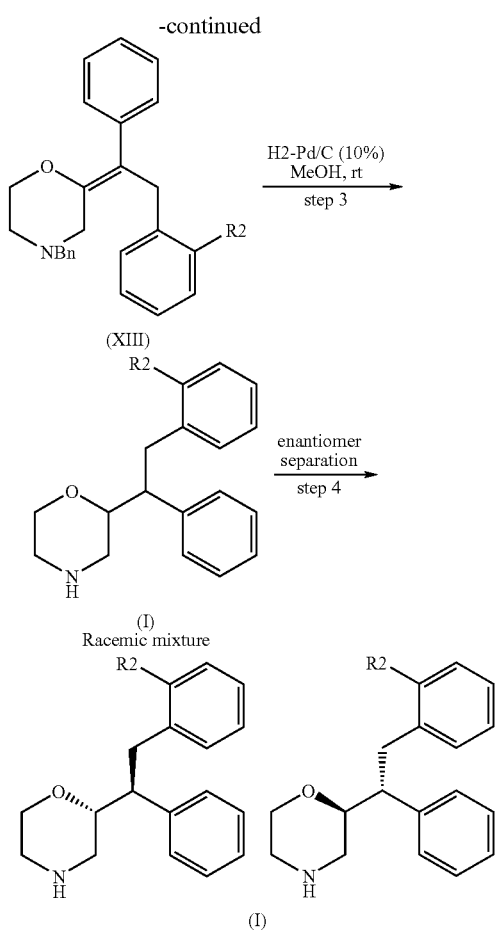

In scheme 2, step 1, (X) is transformed into (XI) using t-BuOK in the presence of 10% H₂O for the deprotonation of the ketone and then the enolate is trapped with N-phenyl-bis(trifluoromethanesulfonimide) to afford the desired E-enoltriflate intermediate (XI). Though other bases could be used (LDA, NaH, sodium methanolate or potassium methanolate) the undesired Z-enoltriflate could be formed, potentially even as the major component so t-BuOK is preferred. The reaction is preferably carried out in THF. Other solvents could be used, such as dichloromethane or tert-butanol, though again the undesired Z-enoltriflate could be formed even as the major component. The presence of water is very important in order to ensure that the reaction works under thermodynamic conditions to favour the E-enoltriflate. It is preferable to let the reaction proceed for up to 20 hours in order to favour the thermodynamic product.

In scheme 2, step 2, (XI) is coupled to (XII) to give (XIII). The reaction is preferably carried out in THF. Other solvents could be used, such as dioxane, DMF and also other palladium catalysts may be employed. The coupling is preferably conducted at reflux for short period of time (30-60 minutes). Longer periods of time may affect the yield.

Additional compounds of the general formula (XIII) wherein R2 is an aryl or heteroaryl group may be obtained by functionalisation of compounds of formula (XIII) wherein R2 is Br or TfO. This may be achieved by a palladium catalysed coupling reaction with the requisite boronic reagent in a manner well known to those skilled in the art.

In scheme 2, step 3, (XIII) is hydrogenated to the saturated and N-deprotected morpholine of formula (I) as a racemic mixture. The reaction is preferably carried in methanol, though other protic solvents could be used like ethanol. The reaction is conducted at room temperature using 0.1 equivalents of catalyst. More catalyst (up to 1:1 w/w) could be used. At this point, the material is a racermic mixture.

The final step is the separation of the racemate into the single enantiomers using chiral HPLC conditions. Other separation conditions could be applied like the transformation of the racemate into a diastereomeric salt by treating the free amine with an enantiomerically pure acid like D-tartaric acid and, finally, conducting the separation by resolution (e.g. fractional crystallization) of the so formed salt.

Another possible route to compounds of formula (I) from a compound of formula (X) is shown in Scheme 3 below. Once again, the nitrogen protecting group is shown as benzyl (Bn) and the group Ar1 is shown as an ortho-substituted phenyl group but in principle other protecting groups and Ar1 groups could also be used:

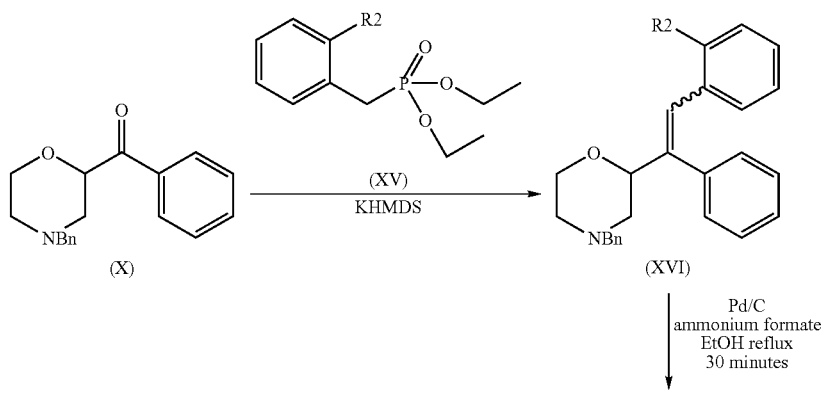

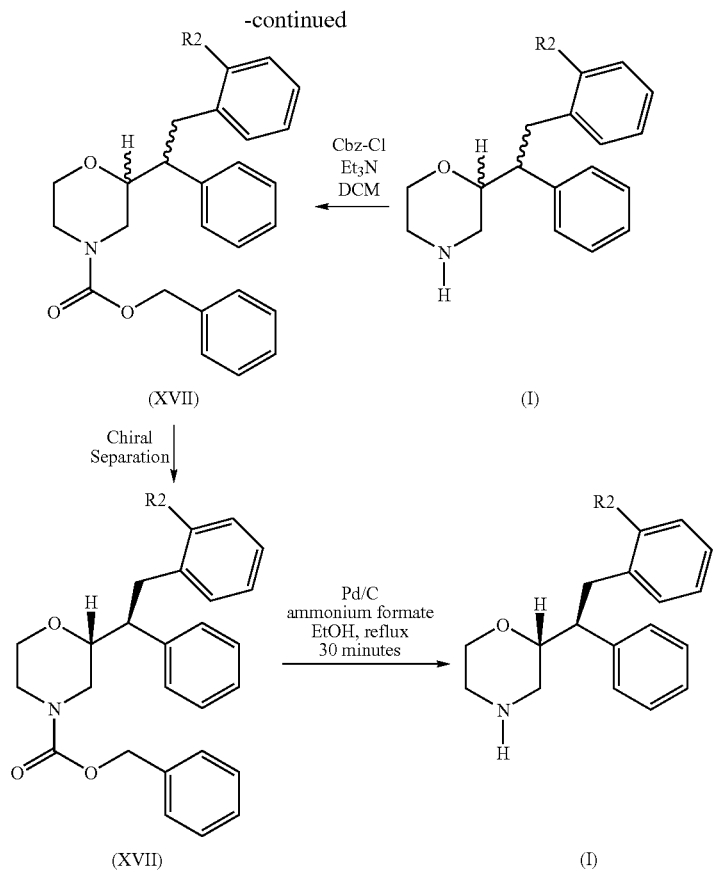

Phosphonate (XV) is pre-reacted with KHMDS in a solvent such as toluene. A solution of the ketone (X) in a solvent such as THF is then added to provide the alkene (XVI). Alternatively, (XVI) may be obtained using a phosphonium ylid generated by reaction of PPh₃ with a benzyl chloride starting material followed by reaction with a strong base such as butyllithium as shown in Scheme 4 below:

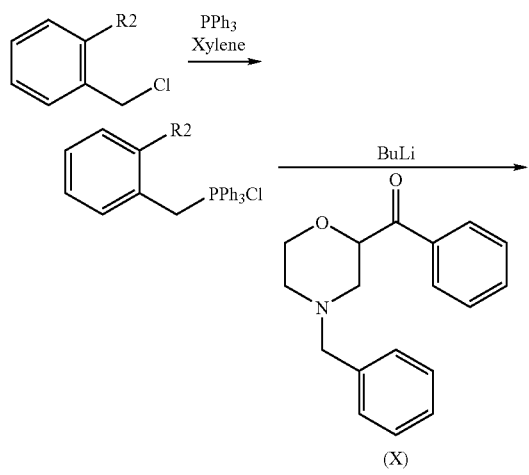

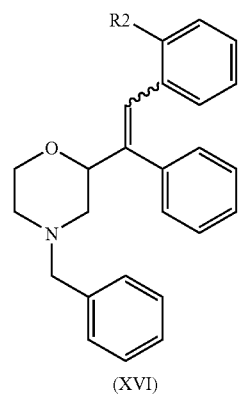

Reduction of (XVI) using palladium on carbon as a catalyst provides compounds of formula (I) which may be resolved into individual enantiomers by generation of the Cbz protected compound of formula (XVII), resolution using, for example, chiral chromatography and deprotection.

Thus, in another embodiment of the present invention there is provided a process for the preparation of compounds of formula (I) comprising the step of deprotecting a compound of the formula (XVIII)

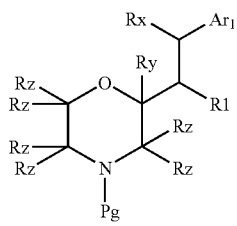

(XVIII)

wherein Pg represents an N-protecting group and all other variables are as defined for formula (I) above, to provide a compound of formula (I), optionally followed by the step of forming a pharmaceutically acceptable salt.

Experimental details for the synthesis of examples of compounds of the present invention are given below. The following abbreviations are used: THF refers to tetrahydrofuran; DMF refers to N,N-dimethylformamide; KHMDS refers to potassium bis(trimethylsilyl)amide, AIBN refers to azo-isobutyronitrile, DMAP refers to dimethylaminopyridine, TBAF refers to tetrabutylamonium fluoride, TBDMSO refers to tert-butyldimethylsilyloxy, NBS refers to N-bromosuccinimide, Tf refers to trifluoromethanesulfonyl, TFA refers to trifluoroacetic acid; RT refers to room temperature, IPA refers to isopropyl alcohol; EtOH refers to ethyl alcohol; MeOH refers to methyl alcohol; $Et_2O$ refers to diethyl ether; BOC or Boc refers to tert-butoxycarbonyl; CBZ or Cbz refers to benzyloxycarbonyl; Bn refers to benzyl; min refers to minutes; h refers to hours; eq refers to equivalents.

(4-Benzyl-morpholin-2-yl)-phenyl-methanone

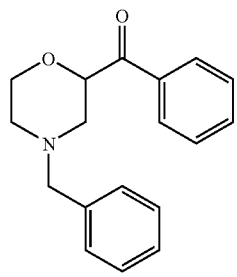

A 1600 L GL reactor under $N_2$ is successively loaded with 2-chloroacrylonitrile (33.2 kg, 379 moles) and toluene (114 L) at 21° C. Then, N-benzylethanolamine (57 kg, 377 moles) is added and the reaction mixture is post-agitated at room temperature for about 17 h. Then, the mixture is diluted with toluene (336 L), cooled down to −12.4° C. and potassium t-butoxide (42.3 kg, 377 moles) is added in portions (10) maintaining −13.7° C. ≦Tmass≦−2.8° C. The mixture is post-agitated at about 0° C. for 2.5 h, quenched by adding ultra pure water (142.5 L) maintaining 2.1° C.≦Tmass≦8.7° C. The aqueous layer (176 kg) is separated after 35 minutes of post-stirring allowing the mixture to reach 15° C. and the toluene layer is washed with ultra pure water (142.5 L) and the aqueous layer (162 kg) is separated. The organic layer is then concentrated under reduced pressure (150 mbars) maintaining Tmass≦60° C. in order to distill 162 kg of toluene. The filtrates are then diluted with toluene (114 L) and treated with $SiO_2$ (Merck silica gel 60, 0.063-0.1 mm, 74.1 kg) under agitation at room temperature for 1.25 h. $SiO_2$ is filtered and rinsed with toluene (2×114 L). Then, the filtrates are concentrated under reduced pressure (150 mbars) maintaining Tmass≦60° C. in order to distill 351.8 kg of toluene (KF: 0.01% w/w $H_2O$).

The solution of 4-Benzyl-morpholine-2-carbonitrile (169.2 kg) is diluted with toluene (157 L) and is cooled to 0° C. and phenylmagnesiumchloride (25 wt. % solution in THF, 213 kg, 389 moles, 1.36 molar equiv.) is slowly added (over 3.5 h) to the reaction mixture, maintaining the temperature at −3° C.≦Tmass≦7° C. The reaction mixture is post-stirred for 2 hours at Tmass=0° C. Then, the quench is performed by adding acetic acid (8.55 L, Tmass=5→4 17.2° C.), post stirring 10 minutes and cooling to 5° C. before adding an acetic acid/water mixture (229 L, 33/67 v/v). During the quench, addition is performed at such a rate that Tmass does not exceed 20° C. (typical Tmass=4.6° C. to 10.4° C.). The mixture is post-agitated overnight at RT and the aqueous layer (285.8 kg) is extracted.

The toluene layer is cooled to 0° C. and a 5 N NaOH aqueous solution (420.1 kg) is slowly added maintaining the temperature at −2.4° C.≦Tmass≦11° C. The reaction mixture is post-stirred for 1 h and the aqueous layer (494.8 kg) is extracted. The toluene layer is concentrated under reduced pressure (50 mbars) maintaining Tmass≦60° C. in order to distill 356.2 kg of toluene and isopropanol (180.4 kg) is added. The toluene is stripped off under reduced pressure (100 mbars) maintaining Tmass≦60° C. in order to distill 186.4 kg of toluene and isopropanol (135 kg) is added again to the mixture. A last distillation of toluene is performed under reduced pressure (50 mbars) maintaining Tmass ≦60° C. in order to distill 131 kg of toluene and isopropanol (49.4 kg) is finally added to the mixture and the solution is stirred at RT until crystallization (17 minutes).

Ultra pure water is added (125.4 L) and the mixture is stirred overnight at RT and cooled down to about 0° C. for 1 hour. The precipitate is filtered and rinsed with a cooled water/isopropanol 50/50 v/v solution (76.6 kg). The wet precipitate is dried under vacuum at Tjack=35° C. for 96 hours to obtain the title compound as an off-white powder with 59% overall yield.

E-Trifluoro-methanesulfonic acid (4-benzyl-morpholin-2-ylidene)-phenyl-methyl ester

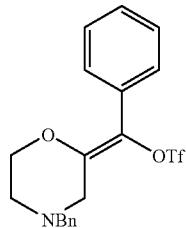

Add Potassium tert-Butoxide 95% (1.06 g, 7.82 mmol) to a solution of (4-Benzyl-morpholin-2-yl)-phenyl-methanone (2 g, 7.11 mmol) and (2.06 g, 7.82 mmol) of 18-Crown-6 in THF (30 ml), under inert atmosphere at 0° C., and stir at this temperature for 15 min and then at room temperature for a period of 45 min. Then add N-Phenyl-bis(trifluoromethanesulfonimide) (3.05 g, 8.54 mmol) and stir at room temperature for 20 h. Remove the solvent, add $Et_2O$ and filter off the suspension. Wash the solid twice with $Et_2O$. Concentrate organic extracts at vacuum and purify the residue by column chromatography on silica gel eluting with $CH_2Cl_2$:hexane, 1:1 to obtain pure E-Trifluoro-methanesulfonic acid (4-benzyl-morpholin-2-ylidene)-phenyl-methyl ester as dense yellow oil, which becomes solid on standing in the freezer: mass spectrum (m/e): 414 (M$^+$+1); $^1$H-NMR (CDCl$_3$, 300 MHz): δ 7.57 (dd, J=1.3 and 8.2 Hz, 2H), 7.43-7.26 (m, 8H), 4.02 (t, J=4.8 Hz, 2H), 3.67 (s, 2H), 3.45 (s, 2H), 2.68 (t, J=4.8 Hz, 2H); $^{13}$C-NMR (CDCl$_3$, 75 MHz): δ 147.2, 136.7, 133.7, 131.4, 130.1, 129.9, 129.7, 129.4, 129.1, 129.0, 128.9, 128.5, 128.1, 128.0, 120.7, 116.5, 68.6, 63.3, 51.5, 50.6.

General Procedure CL A

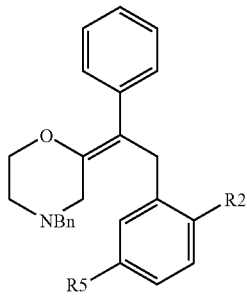

Add 1 eq of E-Trifluoromethanesulfonic acid (4-benzyl-morpholin-2-ylidene)-phenyl-methyl ester and 0.05 eq of tetrakistriphenylphospine to a solution of 1.2 eq of the corresponding organozinc reagent in dry THF (7.5 ml/mmol), under inert atmosphere, and stir at 95° C. for 1 h. Allow the reaction to reach room temperature, treat with $H_2O$ and filter off through celite. Concentrate the liquid at vacuum and purify the residue by column chromatography on silica gel eluting with $CH_2Cl_2$:MeOH, 98:2 to afford the desired coupled derivative as dense pale yellow to yellow oil.

Non commercially available organozinc reagents may be prepared from the corresponding benzyl bromide using the procedure developed by R1 eke et al: J. Org. Chem. 1991, 56, 1445.

Z-4-Benzyl-2-(2-biphenyl-2-yl-1-phenyl-ethylidene)-morpholine

Using the method of General Procedure CL A and using (2-Biphenylylmethyl)zinc bromide (commercially available from Aldrich.)

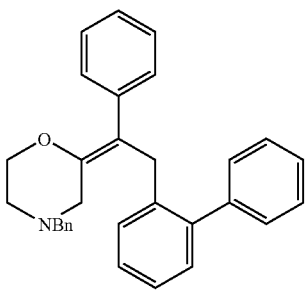

mass spectrum (m/e): 432 (M$^+$+1); $^1$H-NMR (CDCl$_3$, 200 MHz): δ 7.37-7.02 (m, 19H), 3.91-3.84 (m, 2H), 3.53-3.43 (m, 4H), 3.03 (s, 2H), 2.58-2.50 (m, 2H).

Z-4-Benzyl-2-[2-(2-ethoxy-phenyl)-1-phenyl-ethylidene]-morpholine

Using the method of General Procedure CL A and using 2-ethoxybenzylzinc chloride (commercially available from Aldrich.)

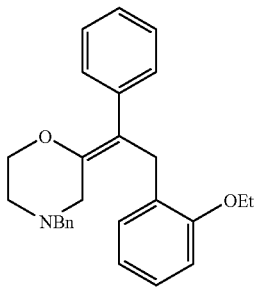

mass spectrum (m/e): 400 (M$^+$+1); $^1$H-NMR (CDCl$_3$, 200 MHz): δ 7.31-7.09 (m, 11H), 6.90-6.75 (m, 3H), 4.00-3.81 (m, 4H), 3.63 (s, 2H), 3.54 (s, 2H), 3.24 (s, 2H), 2,58-2.54 (m, 2H), 1.35 (t, J=7 Hz, 3H).

Z-4-Benzyl-2-[2-(2-bromo-phenyl)-1-phenyl-ethylidene]-morpholine

Using the method of General Procedure CL A and using 2-bromobenzylzinc bromide (commercially available from Aldrich.)

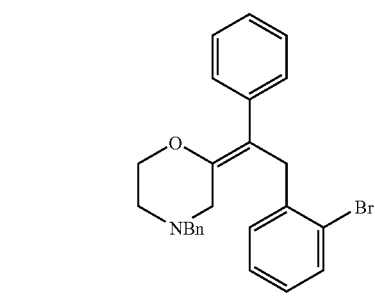

mass spectrum (m/e): 434 (M$^+$+1), 436 (M$^+$+3); $^1$H-NMR (CDCl$_3$, 200 MHz): δ 7.48 (dd, J=1.1 and 7.7 Hz, 1H), 7.30-7.14 (m, 12H), 7.02 (dt, J=2.2 and 7.6 Hz, 1H), 3.93 (t$_{ap}$, J=4.8 Hz, 2H), 3.71 (s, 2H), 3.53 (s, 2H), 3.17 (s, 2H), 2.59 (t$_{ap}$, J=4.8 Hz, 2H).

Z-4-Benzyl-2-[2-(2-isopropyl-phenyl)-1-phenyl-ethylidene]-morpholine

Using the method of General Procedure CL A and using 2-isopropylbenzylzinc bromide.

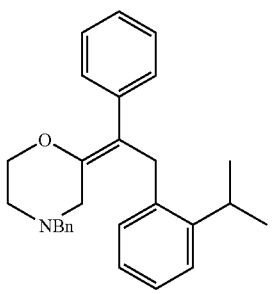

mass spectrum (m/e): 398 (M⁺+1); ¹H-NMR (CDCl₃, 200 MHz): δ 7.33-7.02 (14H), 3,92 (t$_{ap}$, J=4.8 Hz, 2H), 3.65 (s, 2H), 3.53 (s, 2H), 3.17 (s, 2H), 3.05 (sep, J=6.8 Hz, 1H), 2.60 (t$_{ap}$, J=4.8 Hz, 2H), 1.09 (d, J=6.8 Hz, 6H).

The organozinc reagent is not commercially available and is prepared from 1-Bromomethyl-2-isopropyl-benzene. This intermediate is synthesised as follows:

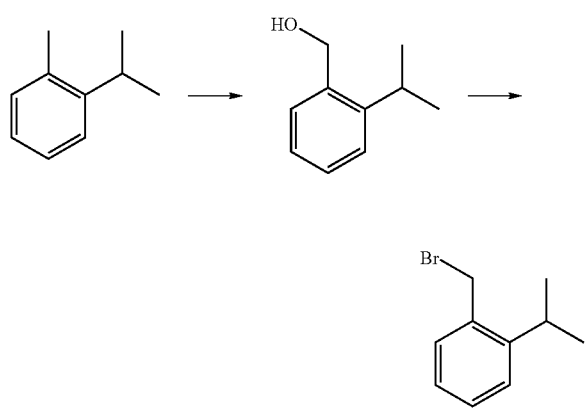

Add 1.7M tert-BuLi (26 ml, 44 mmol) dropwise, at −78° C. under inert atmosphere, to a solution of 1-Iodo-2-iso-propylbenzene (5 g, 20.3 mmol) in 70 ml of dry THF and stir. After 10 min, add Paraformaldehyde (2 g, 66.7 mmol) in a single portion. Stir the reaction at this temperature for 15 min and then at room temperature for 2 h. Add a saturated aqueous solution of NH₄Cl and extract with CH₂Cl₂ three times. Dry the combined organic extracts over Na₂SO₄, filter and concentrate under reduced pressure to give a residue. Purify the residue by column chromatography on silica gel eluting with CH₂Cl₂ to afford pure (2-Isopropyl-phenyl)-methanol as pale purple oil. Add aqueous concentrated HBr (15 ml) to a solution of (2-Isopropyl-phenyl)-methanol (1,93 g, 12.85 mmol) in CH₂Cl₂(15 ml) and stir at room temperature. After 2 h. separate phases and wash the organic one with H₂O; dry over Na₂SO₄ and evaporate at vacuum to obtain a residue. Purify the residue by column chromatography on silica gel eluting with CH₂Cl₂ to obtain 1-Bromomethyl-2-isopropyl-benzene as very pale pink light oil. ¹H-NMR (CDCl₃, 200 MHz): δ 7.33-7.25 (m, 3H), 7.19-7.11 (m, 1H), 4.58 (s, 1H), 3.31 (sep, J=6.8 Hz, 1H), 1.30 (d, J=6.8 Hz, 6H).

Z-4-Benzyl-2-[2-(2-phenoxy-phenyl)-1-phenyl-ethylidene]-morpholine

Using the method of General Procedure CL A and using 2-phenoxybenzylzinc bromide.

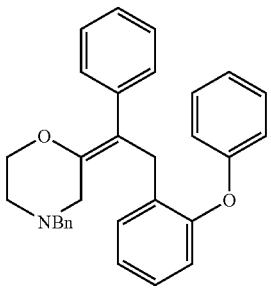

mass spectrum (m/e): 448 (M⁺+1); ¹H-NMR (CDCl₃, 200 MHz): δ 7.35-7.02 (m, 16H), 6.84-6.70 (m, 3H), 3.89 (tap J=4.8 Hz, 1H), 3.62 (s, 2H), 3.51 (s, 2H), 3.18 (s, 2H), 2.57 (t$_{ap}$, J=4.8 Hz, 2H).

The organozinc reagent is not commercially available and is prepared from 1-Bromomethyl-2-phenoxy-benzene. This intermediate is prepared as follows:

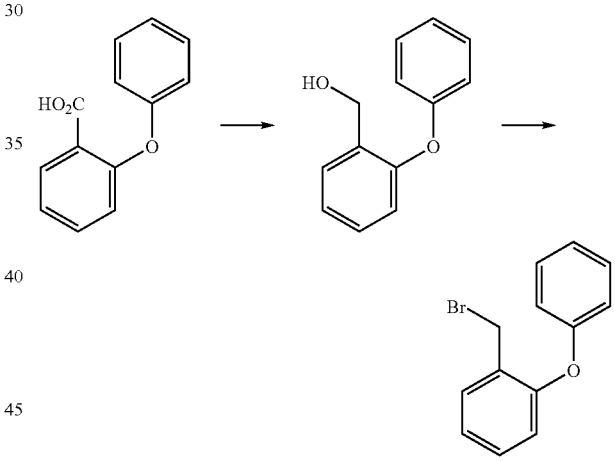

Add 2-Phenoxy-benzoic acid (1 g, 4.67 mmol), in several portions, to a suspension of Lithium aluminium hydride (372 mg, 9.33 mmol) in dry THF (20 ml) at room temperature and stir. After 1 h, add aqueous 1M HCl dropwise carefully, then pour into H₂O and extract three times with Et₂O. Combine the organic phases, dry over Na₂SO₄ and concentrate at vacuum to yield pure (2-Phenoxy-phenyl)-methanol as courless oil. Add aqueous concentrated HBr (16 ml) to a solution of (2-Phenoxy-phenyl)-methanol (900 mg, 4.5 mmol) in CH₂Cl₂ (5 ml) and stir at room temperature. After 1 h. separate the organic phase and wash the aqueous one with CH₂Cl₂. Combine organic phases, wash with H₂, dry over Na₂SO₄ and concentrate at vacuum to obtain a residue. Purify the residue by column chromatography on silica gel eluting with hexane:CH₂Cl₂, 2:1 to afford 1-Bromomethyl-2-phenoxy-benzene as colourless oil. ¹H-NMR (CDCl₃, 200 MHz): δ 7.44-7.01 (m, 8H), 6.84 (d, J=1.2 and 8.0 Hz, 1H), 4.60 (s, 2H).

31

Z-4-Benzyl-2-[2-(5-fluoro-2-methoxy-phenyl)-1-phenyl-ethylidene]-morpholine

Using the method of General Procedure CL A and using 5-fluoro-2-methoxy benzylzinc bromide.

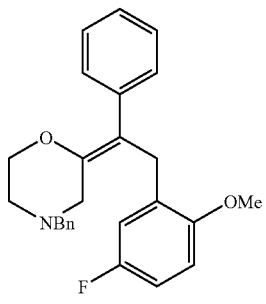

mass spectrum (m/e): 404 (M$^+$+1); $^1$H-NMR (CDCl$_3$, 200 MHz): δ 7.35-7.12 (m, 10H), 6.95 (dd, J=3.0 and 9.5, 1H), 6.89-6.78 (m, 1H), 6.69 (dd, J=4.6 and 8.8 Hz, 1H), 3.93 (t, J=4.8 Hz, 2H), 3.71 (s, 3H), 3.59 (s, 2H), 3.55 (s, 2H), 3.21 (s, 2H), 2.60 (t, J=4.8 Hz, 2H).

The organozinc reagent is not commercially available and is prepared from 2-Bromomethyl-4-fluoro-1-methoxy-benzene. This intermediate is synthesised as follows:

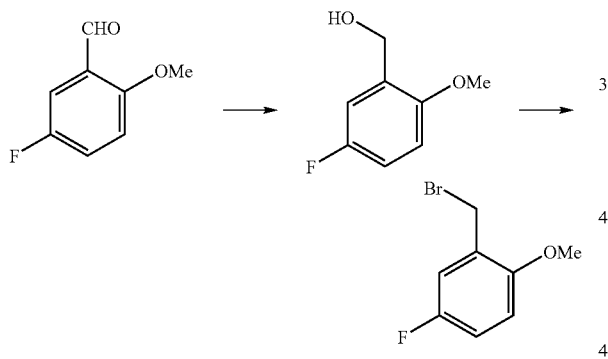

Add Sodium borohydride (540 mg, 13.95 mmol) in portions to a solution of 5-Fluoro-2-methoxy-benzaldehyde (2.15 g, 13.94 mmol) in absolute EtOH (20 ml) and stir at room temperature. After 1 h, evaporate the solvent, dilute the residue in CH$_2$Cl$_2$ and treat with aqueous 3M HCl. Separate the phases, wash the organic one twice with H$_2$O, dry over Na$_2$SO$_4$ and concentrate at vacuum to obtain pure (5-Fluoro-2-methoxy-phenyl)-methanol as white solid. Add aqueous concentrated HBr (15 ml) to a solution of (5-Fluoro-2-methoxy-phenyl)-methanol (1.9 g, 12.17 mmol) in CHCl$_3$ (10 ml) and stir at room temperature. After 1 h, separate the phases, wash the aqueous one with CH$_2$Cl$_2$, combine organic phases, wash with H$_2$O, dry over Na$_2$SO$_4$ and concentrate at vacuum to obtain a residue. Purify the residue by column chromatography on silica gel eluting with hexane to afford 2-Bromomethyl-4-fluoro-1-methoxy-benzene as white solid. $^1$H-NMR (CDCl$_3$, 200 Mz): δ 7.06 (dd, J=3.0 and 8.6 Hz, 1H), 6.98 (m, 1H), 6.81 (dd, J=4.4 and 9.0 Hz, 1H), 4.50 (s, 2H), 3.87 (s, 3H).

32

4-Benzyl-2-{2-[2-(tert-butyl-dimethyl-silanyloxy)-phenyl]-1-phenyl-ethylidene}-morpholine Using the method of general procedure CL A and using 2-tertbutyldimethylsilanyloxy benzyl zinc bromide gives the title comound.

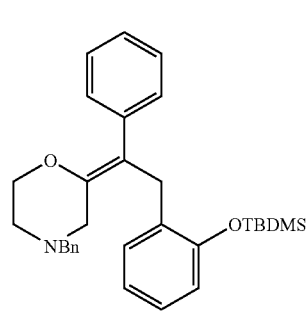

Mass spectrum (m/e): 486 (M$^+$+1)

The organozinc reagent is not commercially available and is prepared from (2-Bromomethyl-phenoxy)-tert-butyl-dimethyl-silane. This intermediate is synthesized as follows:

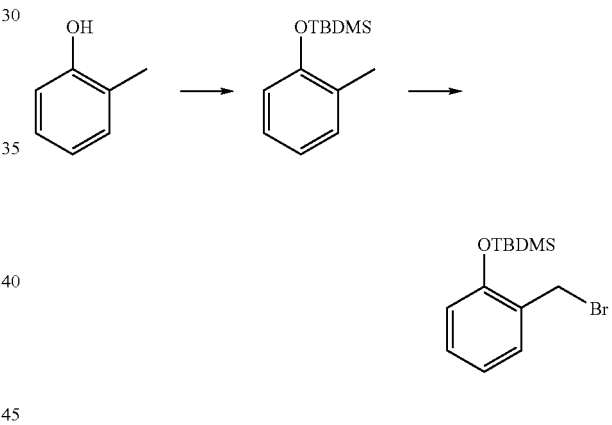

Add TBDMSCl (4.6 g, 30.5 mmol) to a solution of o-cresol (3 g, 28 mmol) and imidazole (2.08 g, 30.5 mmol) in 25 ml of dry DMF and stir at room temperature. After 7 h, pour the reaction into H$_2$O and extract with hexane twice. Combine the organic layers, wash with H$_2$O, dry over Na$_2$SO$_4$, filter and concentrate under reduced pressure to give a residue. Purify the residue by column chromatography on silica gel eluting with hexane to afford pure (1,1-dimethylethyl)dimethyl(2-methylphenoxy)silane as colourless oil. Add AIBN (330 mg, 1.98 mmol) to a solution of NBS (3.87 g, 21.76 mmol) and (1,1-dimethylethyl)dimethyl(2-methylphenoxy)silane (4.4 g, 19.78 mmol) in 100 ml of CCl$_4$ and stir at reflux for 6 h. Concentrate the solvent under reduced pressure, add hexane and filter the solid. Wash the hexane with a saturated aqueous solution of NaHCO$_3$ and H$_2$O. Dry the organic phase over Na$_2$SO$_4$, filter and concentrate under reduced pressure to obtain [2-(bromomethyl)phenoxy](1,1-dimethylethyl)dimethylsilane as colourless oil.

$^1$H-NMR: 7.34 (dd, J=1.8 Hz and J'=7.5 Hz, 1H), 7.19 (dt, J'=1.8 Hz and J=7.8 Hz, 1H), 6.92 (dt, J=0.9 Hz and J'=7.5 Hz), 6.81 (d, J=8.1 Hz, 1H), 4.5 (s, 2H), 1.06 (s, 9H), 0.30 (s, 6H).

General Procedure CL B

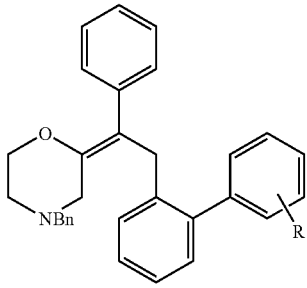

Add Tris(dibenzylideneacetone)dipalladium(0) (0.01 eq) and Tri-tert-butylphosphine (0.025 eq) to a mixture of Z-4-Benzyl-2-[2-(2-bromo-phenyl)-1-phenyl-ethylidene]-morpholine (1 eq), the corresponding Boronic acid (1.1 eq.) and KF (3.3 eq) in dry THF (3 ml/mmol) under inert atmosphere and stir at 95° C. for 1-2 h. Remove the solvent and purify the residue by column chromatography on silica gel eluting with CH$_2$Cl$_2$ and then CH$_2$Cl$_2$/MeOH, 98:2 to afford the desired substituted biphenylmorpholines as pale yellow oils.

4-Benzyl-2-[2-(4'-fluoro-biphenyl-2-yl)-1-phenyl-ethylidene]-morpholine

Using the method of General Procedure CL B and using 4-fluorophenylboronic acid.

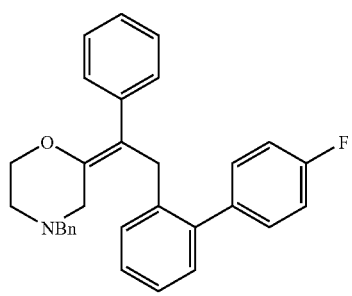

mass spectrum (m/e): 450 (M$^+$+1); $^1$H-NMR (CDCl$_3$, 200 MHz): δ 7.37-6.88 (m, 18H), 3.87 (t$_{ap}$, J=4.8 Hz, 2H), 3.51 (s, 2H), 3.47 (s, 2H), 3.04 (s, 2H), 2.57 (t$_{ap}$, J=4.8 Hz, 2H).

4-Benzyl-2-[2-(3'-fluoro-biphenyl-2-yl)-1-phenyl-ethylidene]-morpholine

Using the method of General Procedure CL B and using 3-fluorophenylboronic acid.

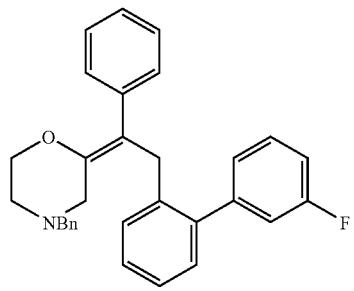

mass spectrum (m/e): 450 (M$^+$+1); $^1$H-NMR (CDCl$_3$, 200 MHz): δ 7.36-6.92 (m, 16H), 6.78 (dt, J=1.4 and 7.8 Hz, 1H), 6.73-6.66 (m, 1H), 3.87 (t$_{ap}$, J=4.8 Hz, 2H), 3.51 (s, 2H), 3.50 (s, 2H), 3.06 (s, 2H), 2.57 (t$_{ap}$, J=4.8 Hz, 2H)

4-Benzyl-2-[1-phenyl-2-(4'-trifluoromethoxy-biphenyl-2-yl)-ethylidene]-morpholine Using the method of General Procedure CL B and using 4-(trifluoromethoxy)phenylboronic acid.

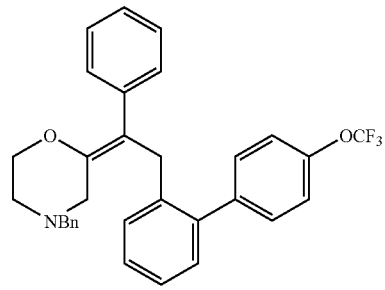

mass spectrum (mn/e): 516 (M$^+$+1); $^1$H-NMR (CDCl$_3$, 200 MHz): δ 7.43-6.95 (m, 18H), 3.87 (t$_{ap}$, J=4.8 Hz, 2H), 3.51 (s, 2H), 3.47 (s, 2H), 3.04 (s, 2H), 2.57 (t$_{ap}$, J=4.8 Hz, 2H)

4-Benzyl-2-[1-Phenyl-2-(3'-trifluoromethoxy-biphenyl-2-yl)-ethylidene]-morpholine Using the method of General Procedure CL B and using 3-(trifluoromethoxy)phenylboronic acid.

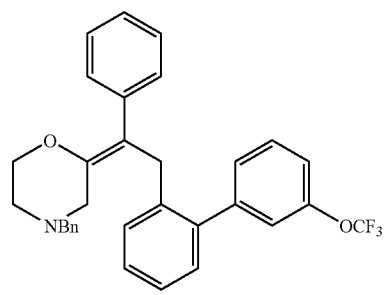

mass spectrum: 516 (M$^+$+1); $^1$H-NMR (CDCl$_3$, 200 MHz): δ 7.40-7.05 (m, 16H), 6.94-6.86 (m, 2H), 3.87 (t$_{ap}$, J=4.8 Hz, 2H), 3.51 (s, 2H), 3.49 (s, 2H), 3.07 (s, 2H), 2.57 (t$_{ap}$, J=4.8 Hz, 2H)

General Procedure CL C

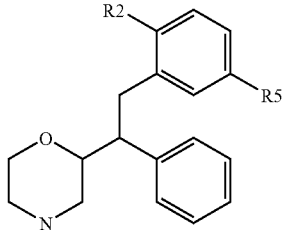

Add 10% Pd/C (0.1-0.5 eq) to a solution or suspension of the requisite Z-4-Benzyl-2-(substituted phenyl-ethylidene)-morpholine in MeOH (10-15 ml/mmol), put a septum to the flask and purge with hydrogen using a balloon for five minutes. Then, stir the mixture at room temperature under H$_2$ atmosphere for 1-3 h. Filter off the reaction through celite, wash twice with MeOH and concentrate the combined methanolic solution at vacuum. Purify the residue by column chromatography on silica gel eluting with CH$_2$Cl$_2$:MeOH, 9:1 to yield the desired morpholines derivatives as dense transparent oils. These compounds are racemic mixtures (R,R and S,S).

| Example N°: | R2 | R5 | Data |
|---|---|---|---|
| 1 | Phenyl | H | mass spectrum(m/e):344(M$^+$+1); $^1$H-NMR(CDCl$_3$, 200MHz): δ 7.35-7.28(m, 3H), 7.15-6.98(m, 9H), 6.78-6.71(m, 2H), 3.86(dt, J=2.6 and 11.2Hz, 1H), 3.62-3.40(m, 3H), 3.16(bs, 1H), 2.90-2.60(m, 4H), 2.43-2.20(m, 2H). |
| 2 | Ethoxy | H | mass spectrum(m/e):312(M$^+$+1); $^1$H-NMR(CDCl$_3$, 200MHz): δ 7.22-6.99(m, 6H), 6.88(dd, J=1.9 and 7.8Hz, 1H), 6.74-6.67(m, 2H), 3.96-3.60(m, 5H), 3.42(dd, J=3.5 and 12.5Hz, 1H), 3.12(bs, 1H), 3.03-2.80(m, 4H), 2.68-2.43(m, 2H), 1.34(t, J=6.9Hz, 3H). |
| 3 | Isopropyl | H | mass spectrum(m/e):310(M$^+$+1); $^1$H-NMR(CDCl$_3$, 200MHz): δ 7.26-6.81(m, 7H), 6.88(dt, J=1.7 and 7.8Hz, 1H), 6.76(dd, J=1.2 and 7.8Hz, 1H), 4.02(d$_{ap}$, J=11.4Hz, 1H), 3.77-3.46(m, 3H), 3.09-2.68(5H), 2.60-2.34(m, 2H), 1.16(d, J=7.0Hz, 3H), 0.97(d, J=6.8Hz, 3H). |
| 4 | Phenoxy | H | HCl salt:mass spectrum(m/e):360(M$^+$+1); $^1$H-NMR(CD$_3$OD, 300MHz): δ 7.35-7.02(m, 10H), 6.96(d, J=7.5Hz, 1H), 6.90-6.79(m, 3H), 6.72(d, J=7.8Hz, 1H), 4.16(dd, J=3.3 and 13.2Hz, 1H), 3.97-3.80(m, 2H), 3.51(dd, J=3.7 and 13.2Hz, 1H), 3.23(d$_{ap}$, J=12.9Hz, 1H), 3.16-3.06(m, 2H), 2.95-2.72(m, 3H). |
| 5 | Methoxy | F | mass spectrum(m/e):316(M$^+$+1); $^1$H-NMR(CDCl$_3$, 200MHz): δ 7.25-7.10(m, 3H), 7.02-6.97(m, 2H), 6.76-6.48(m, 3H), 4.26(bs, 1H), 4.02-3.92(m, 1H), 3.84-3.70(m, 2H), 3.62(s, 3H), 3.39(dd, J=3.8 and 13.0Hz, 1H), 2.94-2.42(m, 6H). |
| 6 | 4-Fluoro-phenyl | H | mass spectrum(m/e):362(M$^+$+1); $^1$H-NMR(CDCl$_3$, 200MHz): δ 7.17-6.86(m, 11H), 6.76-6.70(m, 2H), 3.91-3.84(m, 1H), 3.63-3.38(m, 3H), 2.87-2.61(m, 4H), 2.43-2.20(m, 2H). |
| 7 | 3-Fluoro-phenyl | H | mass spectrum(m/e):362(M$^+$+1); $^1$H-NMR(CDCl$_3$, 300MHz): δ 7.30-6.95(m, 9H), 6.80-6.71(m, 3H), 6.60(dt, J=1-9 and 9.9Hz, 1H), 3.89(d$_{ap}$, J=10.8Hz, 1H), 3.63-3.40(m, 3H), 2.88-2.63(m, 4H), 2.39(dd, J=2.2 and 12.3Hz, 1H), 2.28(dd, J=9.9 and 12.3Hz, 1H), 1.98(bs, 1H). |
| 8 | 4-OCF$_3$-phenyl | H | mass spectrum(m/e):428(M$^+$+1); $^1$H-NMR(CDCl$_3$, 200MHz): δ 7.18-6.90(m, 11H), 6.74-6.68(m, 2H), 3.86(d$_{ap}$, J=11.2Hz, 1H), 3.67-3.40(m, 3H), 2.86-2.56(m, 4H), 2.38(dd, J=2.4 and 12.3Hz, 1H), 2.24(dd, J=9.6 and 12.3Hz, 1H), 2.12(bs, 1H). |
| 9 | 3-OCF$_3$-phenyl | H | mass spectrum(m/e):428(M$^+$+1); $^1$H-NMR(CDCl$_3$, 200MHz): δ 7.36-7.26(m, 1H), 7.21-6.88(m, 10H), 6.75-6.69(m, 2H), 3.86(m, 1H), 3.62-3.41(m, 3H), 2.87-2.58(m, 4H), 2.37(dd, J=2.6 and 12.4Hz, 1H), 2.24(dd, J=9.4 and 12.2Hz, 1H). |

General procedure CL D

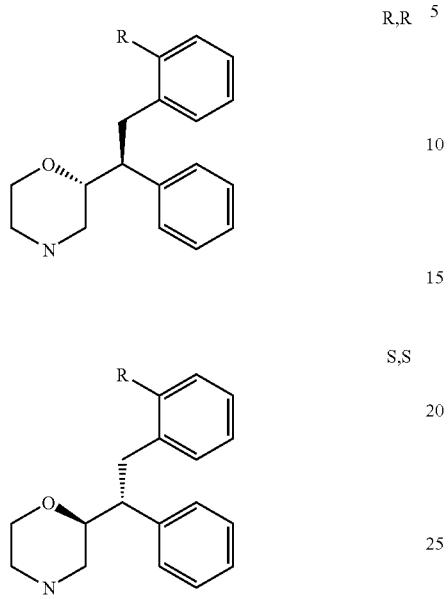

R,R

S,S

The separation of the racemic mixtures (Examples 1-9) into the enantiomers is conducted under three different methods.

Method 1: separate the racemic free base (Examples 1, 2, 6) into the desired enantiomers by a chiralpack AD or chiralcel OD column (10 mm, 4.6×250 mm) under Isocratic mode and flow rates of 0.5-1 ml/min.

Method 2: transform the corresponding racemate into the N-BOC derivative [add 1.1 eq of $(BOC)_2O$ to a solution of 1 eq of Example 8, 3 eq of $Et_3N$ and 0.05 eq of DMAP in dry $CH_2Cl_2$ at 0° C. Stir at room temperature for 3 h. Work up and purification by column chromatography eluting with $CH_2Cl_2$:MeOH, 98:2]. Separation of the N-BOC derivative into the enantiomers by a chiralpack AD or chiralcel OD column (10 mm, 4.6×250 mm) under Isocratic mode and flow rates of 0.5-1 ml/min. Finally, deprotect the corresponding N-BOC enantiomers [aqueous 3M HCl in THF at 60° C. for 7 h. Work; up and purification by column chromatography ($CH_2Cl_2$:MeOH, 95:5)] to affords the desired enantiomers.

Method 3: transform the corresponding racemate into the N-CBZ derivative [add 1.1 eq of ethyl chloroformate to a solution of 1 eq of Examples 3, 4, 5, 7, 9 and 2 eq of $Et_3N$ in dry $CH_2Cl_2$ at 0° C. Stir at room temperature for 1 h. Work up and purify by column chromatography eluting with $CH_2Cl_2$:MeOH, 99:1]. Separation of the N-CBZ derivative into the enantiomers by chiral column a chiralpack AD or chiralcel OD column (10 mm, 4.6×250 mm) under Isocratic mode and flow rates of 0.5-1 ml/min. Finally, deprotect the corresponding N-CBZ enantiomers [$H_2$ and catalyst of Pd/C in MeOH at room temperature for 2 h. Work up and purify by column chromatography eluting with $CH_2Cl_2$:MeOH, 9:1] to yield the desired enantiomers.

EXAMPLE 1

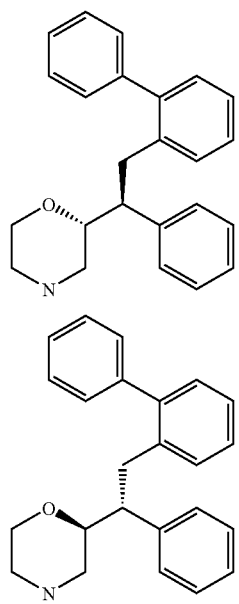

The separation of enantiomers is conducted using method 1 (chiralcell OD; solvent 5 system: hexane-TFA 0.05%/IPA; isocratic mode: 15% B; flow rate: 1 ml/min; E1: 6.0 imin, E2: 8.91 min).

2-(2-Biphenyl-2-yl-1-phenyl-ethyl)-morpholine, Enantiomer 1 mass spectrum (m/e): 344 ($M^+$+1).

2-(2-Biphenyl-2-yl-1-phenyl-ethyl)-morpholine, Enantiomer 2 mass spectrum (m/e): 344 ($M^+$+1).

EXAMPLE 2

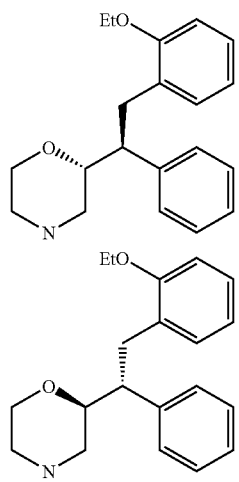

The separation of enantiomers is conducted using method 1 (chiralcell OD; solvent system: hexane/IPA; isocratic mode: 10% B; flow rate: 1 ml/min; E1: 10.79 min, E2: 12.97 min).

2-[2-(2-Ethoxy-phenyl)-1-phenyl-ethyl]-morpholine, Enantiomer 1 mass spectrum (m/e): 312 (M$^+$+1).
2-[2-(2-Ethoxy-phenyl)-1-phenyl-ethyl]-morpholine, Enantiomer 2 mass spectrum (m/e): 312 (M$^+$+1).

EXAMPLE 3

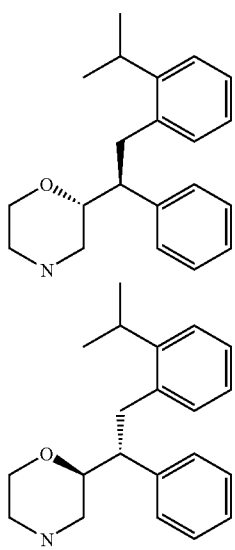

The separation of enantiomers is conducted using method 3 (chiralcell OJ; solvent system: hexane-EtOH; isocratic mode: 15% B; flow rate: 1 ml/min; E1: 5.40 min, E2: 6.70 min).

2-[2-(2-Isopropyl-phenyl)-1-phenyl-ethyl]-morpholine, Enantiomer 1 mass spectrum (m/e): 310 (M$^+$+1).
2-[2-(2-Isopropyl-phenyl)-1-phenyl-ethyl]-morpholine, Enantiomer 2 mass spectrum (m/e): 310 (M$^+$+1).

EXAMPLE 4

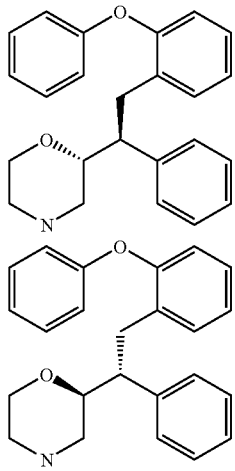

The separation of enantiomers is conducted using method 3 (chiralcell OD; solvent system: hexane-TFA 0.05%/EPA; isocratic mode: 25% B; flow rate: 1 ml/min; E1: 5.96 min, E2: 9.34 min).

2-[2-(2-Phenoxy-phenyl)-1-phenyl-ethyl]-morpholine, Enantiomer 1 mass spectrum (m/e): 360 (M$^+$+1).
2-[2-(2-Phenoxy-phenyl)-1-phenyl-ethyl]-morpholine, Enantiomer 2 mass spectrum (m/e): 360 (M$^+$+1).

EXAMPLE 5

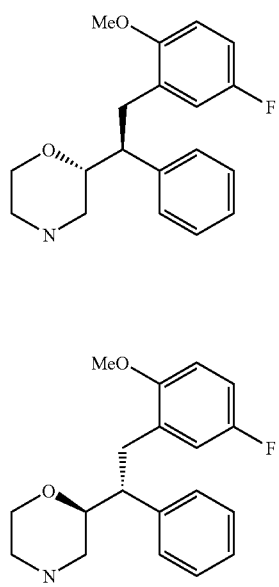

The separation of enantiomers is conducted using method 3 (chiralcell OD; solvent system: hexane-TFA 0.05%/IPA; isocratic mode: 20% B; flow rate: 1 ml/min; E1: 6.32 min, E2: 9.47 min).

2-[2-(5-Fluoro-2-methoxy-phenyl)-1-phenyl-ethyl]-morpholine, Enantiomer 1 mass spectrum (m/e): 316 (M$^+$+1). [α]$_D$ −131° in MeOH
2-[2-(5-Fluoro-2-methoxy-phenyl)-1-phenyl-ethyl]-morpholine, Enantiomer 2 mass spectrum (m/e): 316 (M$^+$+1). [α]$_D$ +130° in MeOH

EXAMPLE 6

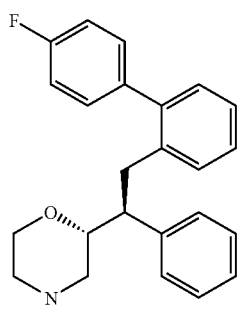

-continued

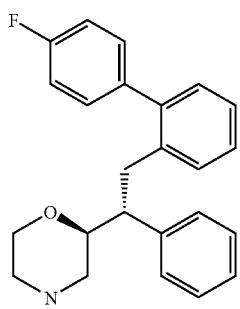

The separation of enantiomers is conducted using method 1 (chiralpak AD; solvent system: hexane/IPA; isocratic mode: 10% B; flow rate: 1 ml/min; E1: 6.15 min, E2: 6.73 min).

2-[2-(4'-Fluoro-biphenyl-2-yl)-1-phenyl-ethyl]-morpholine, Enantiomer 1 mass spectrum (m/e): 362 (M$^+$+1).

2-[2-(4'-Fluoro-biphenyl-2-yl)-1-phenyl-ethyl]-morpholine, Enantiomer 2 mass spectrum (m/e): 362 (M$^+$+1).

EXAMPLE 7

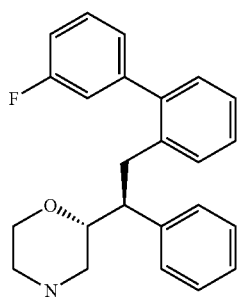

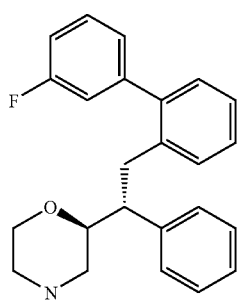

The separation of enantiomers is conducted using method 3 (chiralpak AD; solvent system: hexane-TFA 0.05%/IPA; isocratic mode: 10% B; flow rate: 1 ml/min; E1: 6.12 min, E2: 9.37 min).

2-[2-(3'-Fluoro-biphenyl-2-yl)-1-phenyl-ethyl]-morpholine, Enantiomer 1 mass spectrum (m/e): 362 (M$^+$+1).

2-[2-(3'-Fluoro-biphenyl-2-yl)-1-phenyl-ethyl]-morpholine, Enantiomer 2 mass spectrum (m/e): 362 (M$^+$+1).

EXAMPLE 8

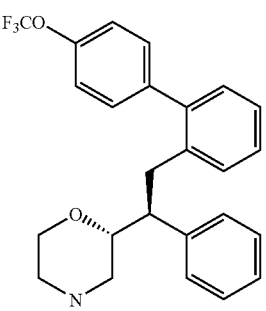

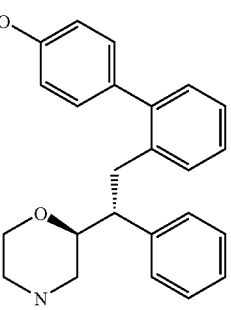

The separation of enantiomers is conducted using method 2 (chiralpak AD; solvent system: hexane/EPA; isocratic mode: 2% B; flow rate: 0.5 ml/min; E1: 10.11 min, E2: 11.03 min).

2-[1-Phenyl-2-(4'-trifluoromethoxy-biphenyl-2-yl)-ethyl]-morpholine, Enantiomer 1 mass spectrum (m/e): 428 (M$^+$+1).

2-[1-Phenyl-2-(4'-trifluoromethoxy-biphenyl-2-yl)-ethyl]-morpholine, Enantiomer 2 mass spectrum (m/e): 428 (M$^+$+1).

EXAMPLE 9

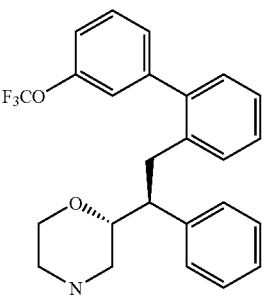

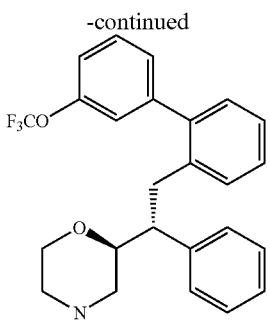

The separation of enantiomers is conducted using method 3 (chiralpak AD; solvent system: hexane/EtOH; isocratic mode: 80% B; flow rate: 1 ml/mn; E1: 3.90 min, E2: 4.41 min).

2-[1-Phenyl-2-(3'-trifluoromethoxy-biphenyl-2-yl)-ethyl]-morpholine, Enantiomer 1 mass spectrum (m/e): 428 (M$^+$+1).

2-[1-Phenyl-2-(3'-trifluoromethoxy-biphenyl-2-yl)-ethyl]-morpholine, Enantiomer 2 mass spectrum (m/e): 428 (M$^+$+1).

2-{2-[2-(tert-Butyl-dimethyl-silanyloxy)-phenyl]-1-phenyl-ethyl}-morpholine

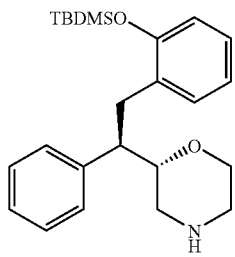

Add Pd/C (10%) (470 mg) to a solution of 4-Benzyl-2-{2-[2-(tert-butyl-dimethyl-silanyloxy)-phenyl]-1-phenyl-ethylidene}-morpholine (470 mg, 0.97 mmol) in 10 ml of MeOH, bubble H$_2$ and stir at room temperature for 4 h. Concentrate the solvent under reduced pressure to give a residue. Purify the residue by column chromatography eluting with CH$_2$Cl$_2$:MeOH 9:1 to afford pure the title compound as colourless oil.

mass spectrum (m/e): 398 (M$^+$+1).

2-{2-[2-(tert-Butyl-dimethyl-silanyloxy)-phenyl]-1-phenyl-ethyl}-morpholine-4-carboxylic acid tert-butyl ester

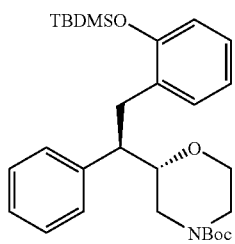

Add (Boc)$_2$O (159 mg, 0.705 mmol), at 0° C., to a solution of 2-{2-[2-(tert-Butyl-dimethyl-silanyloxy)-phenyl]-1-phenyl-ethyl}-morpholine (245 mg, 0.62 mmol), Et$_3$N (0.27 ml, 1.92 mmol) and DMAP (8 mg, 0.064 mmol) in 6 ml of CH$_2$Cl$_2$ and stir at room temperature for 2 h. Concentrate the solvent under reduced pressure and add Et$_2$O. Wash the ethereal phase with HCl/H$_2$O (1M) and then with brine. Dry the organic phase over Na$_2$SO$_4$, filter and remove the solvent to afford impure the title compound, which is used in the next step without further purification.

2-[1-Phenyl-2-(2-trifluoromethanesulfonyloxy-phenyl)-ethyl]-morpholine-4-carboxylic acid tert-butyl ester

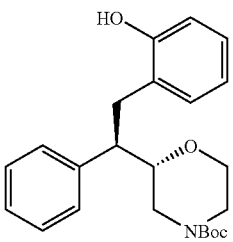

Add TBAF 1M (0.68 ml, 0.68 mmol) to a solution of 2-{2-[2-(tert-Butyl-dimethyl-silanyloxy)-phenyl]-1-phenyl-ethyl}-morpholine-4-carboxylic acid tert-butyl ester (307 mg, 0.62 mmol) in 5 ml of THF and stir at room temperature for 1.5 h. Concentrate the solvent under reduced pressure to give a residue. Purify the residue by column chromatography on silica gel eluting with CH$_2$Cl$_2$:AcOEt 5:1 to afford the title compound as white solid.

mass spectrum (m/e). 382 (M$^+$−1).

2-[1-Phenyl-2-(2-trifluoromethanesulfonyloxy-phenyl)-ethyl]-morpholine-4-carboxylic acid tert-butyl ester

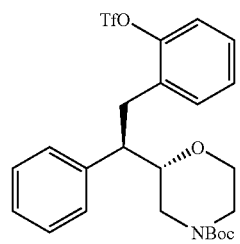

Add NaH 95% (17 mg, 0.68 mmol), at 0° C., to a solution of 2-[1-Phenyl-2-(2-trifluoromethanesulfonyloxy-phenyl)-ethyl]-morpholine-4-carboxylic acid tert-butyl ester (218 mg, 0.568 mmol) in 2 ml of dry DMF and stir for 15 min; then add N-phenyl-bis(trifluoromethanesulfonimide) (224 mg, 0.625 mmol) and stir the reaction at room temperature for 2 h. Add aqueous saturated solution of Na$_2$CO$_3$ and Et$_2$O, separate the organic phase, wash with H$_2$O, dry over Na$_2$SO$_4$, filter and remove the solvent to give a residue. Purify the residue by column chromatography on silica gel eluting with CH$_2$Cl$_2$:AcOEt 98:2 to afford the title compound.

mass spectrum (m/e): 416 (M⁺+1-Boc), 460 (M⁺+1-$^t$Bu); $^1$H-NMR (CDCl$_3$, 300 MHz): 7.20-7.05 (m, 6 H), 6.99-6.95 (m, 3H), 3.94 (dd, J=2.5 and 11.6 HZ, 1H), 3.80 (bs, 1H), 3.60-3.48 (m, 4H), 2.97-2.82 (m, 3H), 2.49 (broad Singlet, 1H), 1.34 (s, 9H).

EXAMPLE 10

2-[1-Phenyl-2-(2-pyridin-3-yl-phenyl)-ethyl]-morpholine dihydrochloride

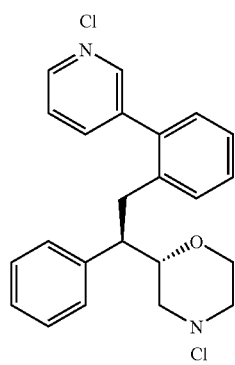

Add palladium diacetate (5.7 mg, 0.024 mmol) and biphenyl-2-yl-di-tert-butyl-phosphane (15 mg, 0.049 mmol) under inert atmosphere to a suspension of 2-[1-Phenyl-2-(2-trifluoromethanesulfonyloxy-phenyl)-ethyl]-morpholine-4-carboxylic acid tert-butyl ester (255 mg, 0.49 mmol), 3-[1,3,2]Dioxaborinan-2-yl-pyridine (91 mg, 0.544 mmol) and K$_3$PO$_4$ (217 mg, 0.99 mmol) in 2 ml of dry DMF and stir at 140° C. for 1.5 h. Add H$_2$O and extract with Et$_2$O (3×20 ml). Combine the organic phases, wash with H$_2$O, dry over Na$_2$SO$_4$ and filter. Concentrate the solvent under reduced pressure and purify the residue by column chromatography eluting with CH$_2$Cl$_2$:MeOH 5% to obtain impure the N-Boc protected title compound.

Add 1 ml of HCl 3M to a solution of the impure N-Boc protected compound in 3 ml of THF and stir at 70° C. for 6 h. Add an aqueous saturated solution of K$_2$CO$_3$ until basic pH and extract with CH$_2$Cl$_2$. Combine the organic layers, dry over Na$_2$SO$_4$ and filter. Concentrate the solvent under reduced pressure to give a residue. Purify the residue by column chromatography on silica gel eluting with CH$_2$Cl$_2$:MeOH 8:2 to afford 15 mg of the title compound as free base (mixture of enantiomers). Transform the free base into the dihydrochloride salt by addition of HCl/Et$_2$O (2M) to a solution of the free base in CH$_2$Cl$_2$. Remove the solvent to obtain the title compound as a white solid.

mass spectrum of dihydrochloride salt (m/e): 345 (M⁺+1); $^1$H-NMR of free base (CDCl$_3$, 300 MHz): 8.50 (broad singlet, 1H), 8.21 (broad singlet, 1H), 7.22-6.98 (m, 9H), 6.70-6.67 (m, 2H), 3.87 (d, J=11.3 Hz, 1H), 3.56 (td, J=3.5 and 10.7 Hz, 1H). 3.48-3.42 (m, 2H), 2.85-2.61 (m, 4H), 2.40-2.22 (m, 2H).

4-Benzyl-2-(1,2-diphenyl-vinyl)-morpholine

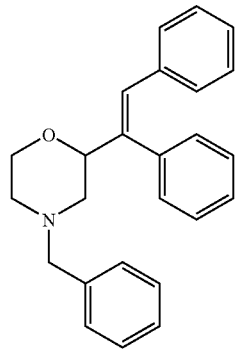

To a cooled solution of KHMDS (0.5M in toluene, 40 ml, 20 mmol) at 0° C. under nitrogen is added diethyl benzyl phosphonate (available from Aldrich Chemical Company) (4.1 ml, 19.7 mmol). The reaction is held at this temperature and stirred for 30 minutes then warmed to room temperature and after 10 minutes a solution of racemic (4-benzyl-morpholin-2-yl)-phenyl-methanone (5.03 g, 17.9 mmol in 25 ml of dry tetrahydrofuran) is added dropwise and the reaction allowed to stir for 30 minutes. At the end of this time the reaction solvent is removed under reduced pressure and replaced with diethyl ether prior to quenching with water. After extraction with diethyl ether and drying (MgSO$_4$) the solvent is again removed under reduced pressure and replaced with methanol at which point a white precipitate forms. The solution is filtered and the cake washed with cold methanol and air-dried. The methanolic solution is further purified using SCX-2 chromatography followed by silica gel chromatography to provide the required material, which is combined with the white precipitate previously obtained.

LCMS (m/e)=356.3 [M+H]⁺@ 4.64 minutes (12 minutes method).

EXAMPLE 11

2-(1,2-Diphenyl-ethyl)-morpholine (mixture of stereoisomers)

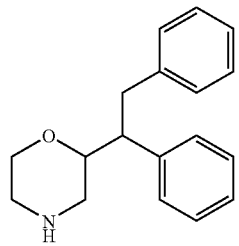

To a methanolic solution of 4-Benzyl-2-(1,2-diphenyl-vinyl)-morpholine (4.9 g, 13.9 mmol) is added ammonium formate (14 g, 222.2 mmol) and 10% Pd—C (5 g). The reaction is stirred under nitrogen and heated at reflux for 30 min then cooled to room temperature and filtered through Celite®. The filtrate is concentrated under reduced pressure and the residue is taken up in methanol and purified by cationic ion exchange resin SCX-2® chromatography. The purified residue (2.9 g, 80%) comprises a 3:1 ratio of diastereoisomers.

LCMS (n/e)=268.1/268.2 (M+1) @ 3.3 and 3.4 minutes (6 minutes method).

2-(1,2-Diphenyl-ethyl)-morpholine-4-carboxylic acid benzyl ester

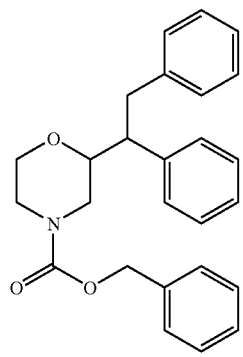

To a solution of 2-(1,2-Diphenyl-ethyl)-morpholine (2 g, 7.49 mmol) in dry dichloromethane (15 ml) at 0° C. under nitrogen atmosphere is added neat triethylamine (2.2 ml, 15.5 mmol, 2.07 equiv.) followed by the addition of neat benzyl chloroformate (1.61 ml, 11.23 mmol, 1.5 equiv.). The reaction is left to reach room temperature over 24 hours and then quenched by addition of a saturated bicarbonate (NaHCO$_3$) aqueous solution. The resulting mixture is extracted with dichloromethane and the resulting organic phases are mixed, dried (MgSO$_4$) and concentrated under reduced pressure to give an oil containing the four possible diastereoisomers (2.3 g, 78%). The diastereoisomers are separated using preparative HPLC, followed by each single enantiomer being resolved by preparative chiral HPLC.

D1 LCMS (m/e)=358.3, 402.2, 424.2 (M+H and M+Na) @ 4.44 minutes (6 minutes method).

D2/E1 LCMS (m/e)=358.3, 402.2, 424.2 (M+H and M+Na) @ 4.86 minutes (6 minutes method).

D2/E2 LCMS (m/e)=358.3, 402.2, 424.2 (M+H and M+Na) @ 4.82 minutes (6 minutes method).

EXAMPLE 11

2-(1,2-diphenyl-ethyl)-morpholine (separate enantiomers)

D1/E1

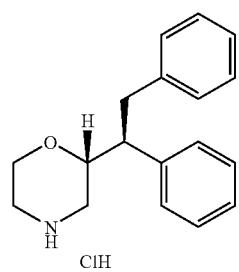

To a solution of 2-(1,2-Diphenyl-ethyl)-morpholine-4-carboxylic acid benzyl ester (416 mg, 1.0 mmol) in ethanol is added ammonium formate (752 mg, 11.9 mmol) and 10% Pd/C (416 mg). The reaction is stirred under nitrogen and heated at reflux for 30 min then cooled and filtered through Celite®. The filtrate is concentrated under reduced pressure and the residue is taken up in methanol and purified firstly by cationic ion exchange resin SCX-2® chromatography and subsequently preparative HPLC chromatography. The purified residue is re-dissolved in a 2M hydrochloric acid in diethyl ether solution and then concentrated under vacuum to give the hydrochloric acid salt (157 mg, 56%).

The above example for D1/E1 is a representative example of the procedures used in the deprotection of D1/E2, D2/E1 and D2/E2.

D1/E1 LCMS (m/e)=268.1 [M+H]$^+$@ 4.21 minutes (12 minutes run). $^1$H NMR (300 MHz, DMSO D$_6$) δ: 2.67 (1 s, 2H), 2.84-3.05 (m, 3H), 3.11-3.18 (m, 1H), 3.27-3.33 (m, 1H), 3.77-3.85 (m, 1H), 3.89-3.96 (m, 1H), 4.06-4.11 (m, 1H), 6.92-7.26 (m, 10H), 9.40 (1 s, 2H).

D1/E2 LCMS (m/e)=268.2 [M+H]$^+$@ 2.20 minutes (6 minutes run). $^1$H NMR (300 MHz, DMSO D$_6$) δ: 2.66-2.68 (m, 2H), 2.83-3.03 (m, 3H), 3.13-3.17 (m, 1H), 3.26-3.27 (m, 1H), 3.73-3.91 (m, 2H), 4.05-4.10 (m, 1H), 6.90-6.93 (m, 2H), 7.01-7.25 (m, 8H), 9.09 (m, 2H).

D2/E1 LCMS (m/e)=268.1 [M+H]$^+$@ 4.27 minutes (12 minutes run). $^1$H NMR (300 MHz, DMSO D$_6$) δ: 2.25-2.36 (m, 1H), 2.67-2.80 (m, 1H), 2.86-2.95 (m, 1H), 3.05-3.19 (m, 3H), 3.61-3.68 (m, 2H), 3.76-3.79 (m, 1H), 4.00-4.06 (m, 1H), 7.12-7.27 (m, 10H), 9.16-9.38 (m, 2H).

D2/E2 LCMS (m/e)=268.2 [M+H]$^+$@ 2.31 minutes (6 minutes run). $^1$H NMR (300 MHz, DMSO D$_6$) δ: 2.25-2.36 (m, 1H), 2.71-2.94 (m, 2H), 3.05-3.18 (m, 4H), 3.58-3.65 (m, 1H), 3.72-3.76 (m, 1H), 4.00-4.05 (m, 1H), 7.10-7.26 (m, 10H), 8.90-9.20 (m, 2H).

(2-Trifluoromethyl-benzyl)-phosphonic acid diethyl ester

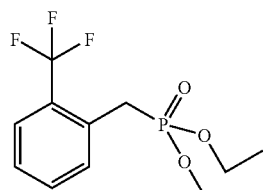

To a suspension of sodium iodide (3.85 g, 25.6 mmol, 1 equiv.) in acetonitrile at room temperature under argon is added neat 1-chloromethyl-2-trifluoromethyl-benzene (commercially available from Acros Organics USA). To the resulting milky suspension is added freshly distilled triethyl phosphite (4.26 g, 25.6 mmol, 1 equiv.) and the resulting solution is stirred overnight at room temperature. After that time further triethyl phosphite (2.13 g, 12.9 mmol, 0.5 equiv.) is added and the reaction mixture heated at reflux for 1 hour. After cooling down to room temperature all volatiles were evaporated under reduced pressure. The residue is taken-up in dichloromethane and filtered through paper and the filtrate is concentrated under reduced pressure to yield the desired material as a clear oil pure enough to be used in the following step without further purification (7.46 g, 98%).

$^1$H NMR (300 MHz, CDCl$_3$ D$_6$) δ: 1.18-1.29 (m, 6H), 3.29-3.46 (m, 2H), 3.95-4.15 (m, 4H), 7.30-7.43 (m, 1H), 7.46-7.58 (m, 1H), 7.61-7.78 (m, 2H).

4-Benzyl-2-[2-Phenyl-2-(2-trifluoromethyl-phenyl)-vinyl]-morpholine

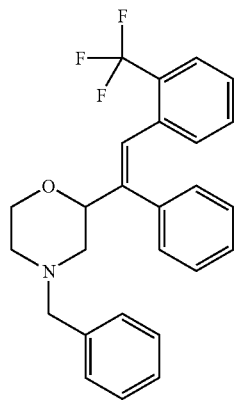

To a cooled solution of KHMDS (0.5M in toluene, 50 ml, 25 mmol) at 0° C. in dry tetrahydrofuran (70 ml) under nitrogen is added freshly prepared neat (2-trifluoromethyl-benzyl)-phosphonic acid diethyl ester (5.7 ml, 25 mmol, 1 equiv.). The reaction is warmed to room temperature over 1 hour and then racemic (4-benzyl-morpholin-2-yl)-phenyl-methanone (7 g, 25 mmol in 25 ml of dry tetrahydrofuran) is added dropwise. The reaction is left at room temperature and stirred for 2 hours. At the end of this time the reaction solvent is removed under reduced vacuum and replaced with diethyl ether prior to quenching with water. After extraction with diethyl ether and drying (MgSO$_4$) the solvent is again removed under reduced pressure. The resulting residue is purified by column chromatography on silica gel to yield a colourless oil (6.5 g, 61%).

FIA (m/e)=424.1 [M+H]$^+$.

EXAMPLE 12

2-[1-Phenyl-2-(2-trifluoromethyl-phenyl)-ethyl]-morpholine (mixture of stereoisomers)

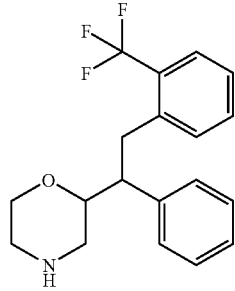

The procedure involving the one pot catalytic hydrogenation/debenzylation sequence followed for the synthesis of 2-(1,2-Diphenyl-ethyl)-morpholine (see above) is used without major modification to yield the title compound as a mixture of four isomers that were used in the next step without further separation.

FIA (m/e)=336.1 [M+H]$^+$.

2-[1-Phenyl-2-(2-trifluoromethyl-phenyl)-ethyl]-morpholine-4-carboxylic acid benzyl ester

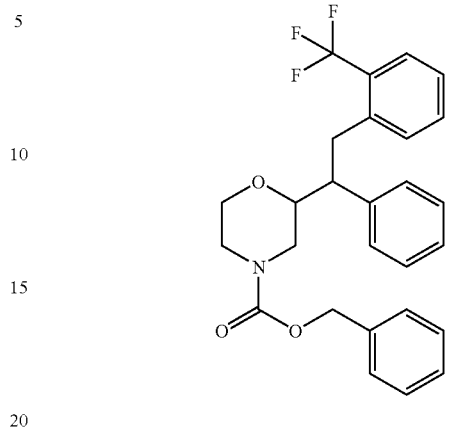

The procedure involving the one pot protection/separation followed for the synthesis of 2-(1,2-Diphenyl-ethyl)-morpholine-4-carboxylic acid benzyl ester (see above) is used without major modification to yield the four possible stereoisomers of the title compound.

D1/E2 LCMS (m/e)=426.2, 470.2, 492.3 (M+H and M+Na) @ 4.99 minutes (6 minutes method).

D2/E1 LCMS (m/e)=426.2, 470.2, 492.3 (M+H and M+Na) @ 5.09 minutes (6 minutes method).

D2/E2 LCMS (mn/e)=426.2, 470.2, 492.3 (M+H and M+Na) @ 5.08 minutes (6 minutes method).

EXAMPLE 12

2-[1-Phenyl-2-(2-trifluoromethyl-phenyl)-ethyl]-morpholine (separate enantiomers)

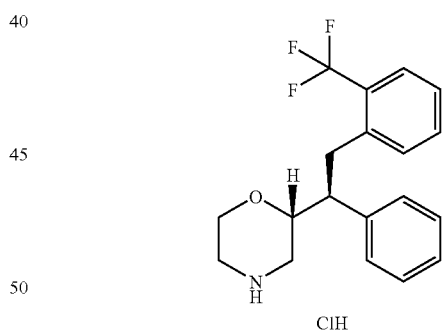

The procedure followed for the synthesis of 2-(1,2-Diphenyl-ethyl)-morpholine (see above) is used without major modification to yield the four possible stereoisomers of the title compound.

E1/D1 LCMS (m/e)=336.1 [M+H]$^+$@ 4.87 minutes (12 minutes run). $^1$H NMR (300 MHz, DMSO D$_6$) δ: 2.60-2.80 (m, 2H), 2.89-3.24 (m, 4H), 3.50-3.67 (m, 1H), 3.75-3.90 (m, 1H), 3.95-4.20 (m, 2H), 6.95-7.06 (m, 1H), 7.10-7.40 (m, 7H), 7.51-7.65 (m, 1H), 9.11 (bs, 2H).

E2/D1 LCMS (m/e)=336.2 [M+H]$^+$@ 2.67 minutes (6 minutes run). $^1$H NMR (300 MHz, DMSO D$_6$) δ: 2.62-2.72 (m, 2H), 2.91-3.18 (m, 4H), 3.55-3.59 (m, 1H), 3.75-3.82 (m, 1H), 3.95-4.10 (m, 2H), 6.98-7.00 (m, 1H), 7.12-7.34 (m, 7H), 7.55-7.58 (m, 1H), 9.12 (bs, 2H).

E1/D2 LCMS (m/e)=336.1 [M+H]$^+$@ 4.98 minutes (12 minutes run). $^1$H NMR (300 MHz, DMSO D$_6$) δ: 2.19-2.29 (m, 1H), 2.67-2.81 (m, 1H), 3.07-3.23 (m, 4H), 3.29-3.38 (m, 1H), 3.70-3.78 (m, 1H), 3.86-3.90 (m, 1H), 4.03-4.12 (m, 1H), 7.20-7.31 (m, 6H), 7.36-7.41 (m, 1H), 7.49-7.54 (m, 1H), 7.65-7.68 (m, 1H), 9.34-9.50 (m, 2H).

E2/D2 LCMS (m/e)=336.1 [M+H]$^+$@ 4.88 minutes (12 minutes run). $^1$H NMR (300 MHz, DMSO D$_6$) δ: 2.20-2.28 (m, 1H), 2.73-2.80 (m, 1H), 3.07-3.23 (m, 4H), 3.29-3.35 (m, 1H), 3.69-3.77 (m, 1H), 3.86-3.90 (m, 1H), 4.03-4.09 (m, 1H), 7.20-7.31 (m, 6H), 7.36-7.41 (m, 1H), 7.49-7.54 (m, 1H), 7.65-7.68 (m, 1H), 9.20-9.60 (1 s, 2H).

The pharmacological profile of the present compounds may be demonstrated as follows. All of the exemplified compounds above have been found to exhibit a K$_i$ value less than 1 μm at the norepinephrine transporter as determined using the scintillation proximity assay described below. Furthermore, all of the exemplified compounds above have been found to inhibit the norepinephrine transporter to a greater extent than the serotonin and dopamine transporters using the scintillation proximity assays as described below.

Generation of Stable Cell-lines Expressing the Human Dopamine, Norepinephrine and Serotonin Transporters Standard molecular cloning techniques are used to generate stable cell-lines expressing the human dopamine, norepinephrine and serotonin transporters. The polymerase chain reaction (PCR) is used in order to isolate and amplify each of the three full-length cDNAs from an appropriate cDNA library. Primers for PCR are designed using the following published sequence data:

Human dopamine transporter: GenBank M95167. Reference: Vandenbergh D J, Persico A M and Uhl GR. A human dopamine transporter cDNA predicts reduced glycosylation, displays a novel repetitive element and provides racially-dimorphic TaqI RFLPs. Molecular Brain Research (1992) volume 15, pages 161-166.

Human norepinephrine transporter: GenBank M65105. Reference: Pacholczyk T, Blakely, R D and Amara S G. Expression cloning of a cocaine- and antidepressant-sensitive human noradrenaline transporter. Nature (1991) volume 350, pages 350-354.

Human serotonin transporter: GenBank L05568. Reference: Ramamoorthy S, Bauman A L, Moore K R, Han H, Yang-Feng T, Chang A S, Ganapathy V and Blakely R D. Antidepressant- and cocaine-sensitive human serotonin transporter: Molecular cloning, expression, and chromosomal localization. Proceedings of the National Academy of Sciences of the USA (1993) volume 90, pages 2542-2546.

The PCR products are cloned into a mammalian expression vector (eg pcDNA3.1 (Invitrogen)) using standard ligation techniques. The constructs are then used to stably transfect HEK293 cells using a commercially available lipofection reagent (Lipofectamine™—Invitrogen) following the manufacture's protocol.

Scintillation Proximity Assays for Determining the Affinity of Test Ligands at the Norepinephrine Transporter.

The compounds of the present invention are norepinephrine reuptake inhibitors, and possess excellent activity in, for example, a scintillation proximity assay (e.g. J. Gobel, D. L. Saussy and A. Goetz, J. Pharmacol. Toxicolo. (1999), 42, 237-244). Thus $^3$H-nisoxetine binding to norepinephrine reuptake sites in a cell line transfected with DNA encoding human norepinephrine transporter binding protein is used to determine the affinity of ligands at the norepinephrine transporter.

Membrane Preparation:

Cell pastes from large scale production of HEK-293 cells expressing cloned human norepinephrine transporters are homogenized in 4 volumes 50 mM Tris-HCl containing 300 mM NaCl and 5 nM KCl, pH 7.4. The homogenate is centrifuged twice (40,000 g, 10 min, 4° C.) with pellet re-suspension in 4 volumes of Tris-HCl buffer containing the above reagents after the first spin and 8 volumes after the second spin. The suspended homogenate is centrifuged (100 g, 10 min, 4° C.) and the supernatant kept and re-centrifuged (40, 000 g, 20 min, 4° C.). The pellet is resuspended in Tris-HCl buffer containing the above reagents along with 10% w/v sucrose and 0.1 mM phenylmethylsulfonyl fluoride (PMSF). The membrane preparation is stored in aliquots (1 ml) at −80° C. until required. The protein concentration of the membrane preparation is determined using a bicinchoninic acid (BCA) protein assay reagent kit (available from Pierce).

[$^3$H]-Nisoxetine Binding Assay:

Each well of a 96 well microtitre plate is set up to contain the following:

| | |
|---|---|
| 50 μl | 2 nM [N-methyl-$^3$H]-Nisoxetine hydrochloride (70-87 Ci/mmol, from NEN Life Science Products) |
| 75 μl | Assay buffer (50 mM Tris-HCl pH 7.4 containing 300 mM NaCl and 5 mM KCl) |
| 25 μl | Test compound, assay buffer (total binding) or 10 μM Desipramine HCl (non-specific binding) |
| 50 μl | Wheatgerm agglutinin coated poly (vinyltoluene) (WGA PVT) SPA Beads (Amersham Biosciences RPNQ0001) (10 mg/ml) |
| 50 μl | Membrane (0.2 mg protein per ml) |

The microtitre plates are incubated at room temperature for 10 hours prior to reading in a Trilux scintillation counter. The results are analysed using an automatic spline fitting programme (Multicalc, Packard, Milton Keynes, UK) to provide Ki values for each of the test compounds.

Serotonin Binding Assay

The ability of a test compound to compete with [$^3$H]-citalopram for its binding sites on cloned human serotonin transporter containing membranes is used as a measure of test compound ability to block serotonin uptake via its specific transporter (Ramamoorthy, S., Giovanetti, E., Qian, Y., Blakely, R., (1998) J. Biol. Chem. 273, 2458).

Membrane Preparation:

Membrane preparation is essentially similar to that for the norepinephrine transporter containing membranes as described above. The membrane preparation is stored in aliquots (1 ml) at −70° C. until required. The protein concentration of the membrane preparation is determined using a BCA protein assay reagent kit.

[$^3$H]-Citalopram Binding Assay:

Each well of a 96 well microtitre plate is set up to contain the following:

| | |
|---|---|
| 50 μl | 2 nM [$^3$H]-Citalopram (60-86 Ci/mmol, Amersham Biosciences) |
| 75 μl | Assay buffer (50 mM Tris-HCl pH 7.4 containing 150 mM NaCl and 5 mM KCl) |
| 25 μl | Diluted compound, assay buffer (total binding) or 100 μM Fluoxetine (non-specific binding) |
| 50 μl | WGA PVT SPA Beads (40 mg/ml) |
| 50 μl | Membrane preparation (0.4 mg protein per ml) |

The microtitre plates are incubated at room temperature for 10 hours prior to reading in a Trilux scintillation counter. The results are analysed using an automatic spline fitting programme (Multicalc, Packard, Milton Keynes, UK) to provide Ki (nM) values for each of the test compounds.

Dopamine Binding Assay

The ability of a test compound to compete with [$^3$H]-WIN35,428 for its binding sites on human cell membranes containing cloned human dopamine transporter has been used as a measure of the ability of such test compounds to block dopamine uptake via its specific transporter (Ramamoorthy et al 1998 supra).

Membrane Preparation:

Is essentially the same as for membranes containing cloned human serotonin transporter as described above.

[$^3$H]-WIN35,428 Binding Assay:

Each well of a 96well microtitre plate is set up to contain the following:

| | |
|---|---|
| 50 µl | 4 nM [$^3$H]-WIN35,428 (84-87 Ci/mmol, from NEN Life Science Products) |
| 75 µl | Assay buffer (50 mM Tris-HCl pH 7.4 containing 150 mM NaCl and 5 mM KCl) |
| 25 µl | Diluted compound, assay buffer (total binding) or 100 µM Nomifensine (non-specific binding) |
| 50 µl | WGA PVT SPA Beads (10 mg/ml) |
| 50 µl | Membrane preparation (0.2 mg protein per ml.) |

The microtitre plates are incubated at room temperature for 120 minutes prior to reading in a Trilux scintillation counter. The results are analysed using an automatic spline fitting programme (Multicalc, Packard, Milton Keynes, UK) to provide Ki values for test compounds.

Acid Stability

The acid stability of a compound according to the present invention may be determined as a solution in buffer at 6 different pH values (HCl 0.1N, pH 2, pH 4, pH 6, pH 7, and pH 8) at 40° C. over a time course of 72 hours. Samples may be taken at the beginning of the study and after 3, 6 and 24 hours and analysed by capillary electrophoresis. The original sample used in the study may contain 0.8% of the undesired epimer as internal standard. If the tested compound is chemically and configurationally stable under acidic conditions the samples taken at the different time points during the study should not show any significant change in the percentage of the undesired epimer.

In Vitro Determination of the Interaction of Compounds with CYP2D6 in Human Hepatic Microsomes Cytochrome P450 2D6 (CYP2D6) is a mammalian enzyme which is commonly associated with the metabolism of around 30% of pharmaceutical compounds. Moreover, this enzyme exhibits genetic polymorphism, resulting in the presence of both normal and poor metabolizers in the population. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) are acquired from Human Biologics (Scottsdale, Ariz., USA). Quinidine and β-NADPH (β-Nicotinamide Adenine Dinucleotide Phosphate, reduced from, tetrasodium salt) are purchased from Sigma (St Louis, Mo., USA). All the other reagents and solvents are of analytical grade. A stock solution of the new chemical entity (NCE) is prepared in a mixture of Acetonitrile/Water to reach a final concentration of acetonitrile in the incubation below 0.5%.

The microsomal incubation mixture (total volume 0.1 mL) contains the NCE (4 µM), β-NADPH (1 mM), microsomal proteins (0.5 mg/mL), and Quinidine (0 or 2 µM) in 100 mM sodium phosphate buffer pH 7.4. The mixture is incubated for 30 minutes at 37° C. in a shaking waterbath. The reaction is terminated by the addition of acetonitrile (75/µL). The samples are vortexed and the denaturated proteins are removed by centrifugation. The amount of NCE in the supernatant is analyzed by liquid chromatography /mass spectrometry (LC/MS) after addition of an internal standard. A sample is also taken at the start of the incubation (t=0), and analysed similarly.

Analysis of the NCE is performed by liquid chromatography /mass spectrometry. Ten µL of diluted samples (20 fold dilution in the mobile phase) are injected onto a Spherisorb CN Column, 5 µM and 2.1 mm×100 mm (Waters corp. Milford, Mass., USA). The mobile phase consisting of a mixture of Solvent A/Solvent B, 30/70 (v/v) is pumped (Alliance 2795, Waters corp. Milford, Mass., USA) through the column at a flow rate of 0.2 ml/minute. Solvent A and Solvent B are a mixture of ammonium formate $5.10^{-3}$ M pH 4.5/methanol in the proportions 95/5 (v/v) and 10/90 (v/v), for solvent A and solvent B, respectively. The NCE and the internal standard are quantified by monitoring their molecular ion using a mass spectrometer ZMD or ZQ (Waters-Micromass corp, Machester, UK) operated in a positive electrospray ionisation.

The extent of CYP2D6 involvement (% of CYP2D6 involvement) is calculated comparing the extent of metabolism in absence and in presence of quinidine in the incubation.

The extent of metabolism without inhibitor (%) is calculated as follows:

$$\frac{(NCE \text{ response in samples without inhibitor})\text{time } 0 - (NCE \text{ response in samples without inhibitor})\text{time } 30}{(NCE \text{ response in samples without inhibitor})\text{time } 0} \times 100$$

The extent of metabolism with inhibitor (%) is calculated as follows:

$$\frac{(NCE \text{ response in samples without inhibitor})\text{time } 0 - (NCE \text{ response in samples with inhibitor})\text{time } 30}{(NCE \text{ response in samples without inhibitor})\text{time } 0} \times 100$$

where the NCE response is the area of the NCE divided by the area of the internal standard in the LC/MS analysis chromatogram, time0 and time30 correspond to the 0 and 30 minutes incubation time.

The % of CYP2D6 involvement is calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an $IC_{50}$ higher than 6 µM for CYP2D6 activity, the $IC_{50}$ being the concentration of the compound that gives 50% of inhibition of the CYP2D6 activity.

Material and Methods:

Human liver microsomes (mixture of 20 different donors, mixed gender) are acquired from Human Biologics (Scottsdale, Ariz.). β-NADPH is purchased from Sigma (St Louis, Mo.). Bufuralol is purchased from Ultrafine (Manchester, UK). All the other reagents and solvents are of analytical grade.

Microsomal incubation mixture (total volume 0.1 mL) contains bufuralol 10 µM, β-NADPH (2 mM), microsomal proteins (0.5 mg/mL), and the new chemical entity (NCE) (0, 5, and 25 µM) in 100 mM sodium phosphate buffer pH 7.4. The mixture is incubated in a shaking waterbath at 37° C. for 5 minutes. The reaction is terminated by the addition of methanol (75 µL). The samples are vortexed and the denaturated proteins are removed by centrifugation. The supernatant is analyzed by liquid chromatography connected to a fluorescence detector. The formation of the 1'-hydroxybufuralol is monitored in control samples (0 µM NCE) and in the samples incubated in presence of the NCE. The stock solution of NCE is prepared in a mixture of Acetonitrile/Water to reach a final concentration of acetonitrile in the incubation below 1.0%.

The determination of 1'hydroxybufuralol in the samples is performed by liquid chromatograhy with fluorimetric detection as described below. Twenty five µL samples are injected onto a Chromolith Performance RP-18e column (100 mm×4.6 mm) (Merck KGAa, Darmstadt, Germany). The mobile phase, consisting of a mixture of solvent A and solvent B whose proportions change according the following linear gradient, is pumped through the column at a flow rate of 1 ml/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consist of a mixture of 0.02 M potassium dihydrogenophosphate buffer pH3/methanol in the proportion 90/10 (v/v) for solvent A and 10/90 (v/v) for solvent B. The run time is 7.5 minutes. Formation of 1'-hydroxybufuralol is monitored by fluorimetric detection with extinction at λ 252 nm and emission at λ 302 nm.

The $IC_{50}$ of the NCE for CYP2D6 is calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

$$\frac{(1'\text{-hydroxybufuralol formed without inhibitor}) - (1'\text{-hydroxybufuralol formed with inhibitor})}{(1'\text{-hydroxybufuralol area formed without inhibitor})} \times 100$$

The $IC_{50}$ is calculated from the percent inhibition of the formation of the 1'-hydroxybufuralol as follows (assuming competitive inhibition):

$$\frac{NCE \text{ Concentration} \times (100 - \text{Percent of inhibition})}{\text{Percent of inhibition}}$$

The $IC_{50}$ estimation is assumed valid if inhibition is between 20% and 80% (Moody G C, Griffin S J, Mather A N, McGinnity D F, Riley R J. 1999. Fully automated analysis of activities catalyzed by the major human liver cytochrome P450 (CYP) enzymes: assessment of human CYP inhibition potential. Xenobiotica, 29(1): 53-75).

The invention claimed is:

1. A compound of formula (V)

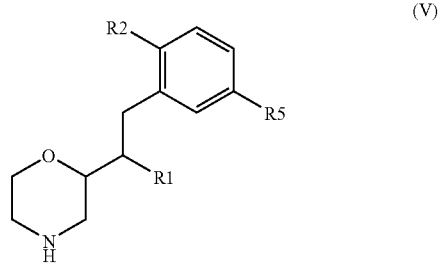

wherein,

R1 is $(CH_2)_n$Ar2 wherein n is 0 and Ar2 is a phenyl ring optionally substituted with 1 or 2 substituents each independently selected from C1-C4 alkyl optionally substituted with 1, 2 or 3 halogen atoms, C1-C4 alkoxy optionally substituted with 1, 2 or 3 halogen atoms, halo and hydroxy;

R2 is C1-C4 alkyl optionally substituted with 1, 2 or 3 fluorine atoms, C1-C4 alkoxy optionally substituted with 1, 2 or 3 fluorine atoms, phenyl optionally substituted with 1, 2 or 3 substituents each independently selected from fluorine and trifluoromethoxy, pyridyl or phenoxy; and R5 is H or F;

or a pharmaceutically acceptable salt thereof.

2. The compound according to claim 1 of formula (VI)

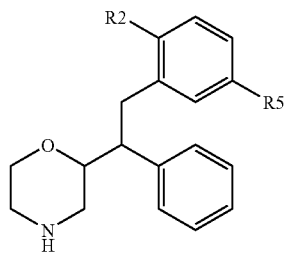

wherein,

R2 is C1-C4 alkyl optionally substituted with 1, 2 or 3 fluorine atoms, C1-C4 alkoxy optionally substituted with 1, 2 or 3 fluorine atoms, phenyl optionally substituted with 1, 2 or 3 substituents each independently selected from fluorine and trifluoromethoxy, pyridyl or phenoxy; and R5 is H or F; or a pharmaceutically acceptable salt thereof.

3. A pharmaceutical composition comprising a compound as claimed in claim 1, or a pharmaceutically acceptable salt thereof, together with a pharmaceutically acceptable diluent, excipient or carrier.

\* \* \* \* \*